(12) United States Patent
Geisert et al.

(10) Patent No.: US 8,486,082 B2
(45) Date of Patent: Jul. 16, 2013

(54) APPARATUS FOR DIMENSIONING CIRCUMFERENCE OF CAVITY FOR INTRODUCTION OF A PROSTHETIC IMPLANT

(75) Inventors: Christophe Geisert, Hufingen (DE); Eduard Kufeld, Tuttlingen (DE)

(73) Assignee: Replication Medical, Inc., Cranbury, NJ (US)

( * ) Notice: Subject to any disclaimer, the term of this patent is extended or adjusted under 35 U.S.C. 154(b) by 1590 days.

(21) Appl. No.: 11/999,400

(22) Filed: Dec. 5, 2007

(65) Prior Publication Data
US 2008/0147076 A1    Jun. 19, 2008

Related U.S. Application Data

(60) Provisional application No. 60/874,618, filed on Dec. 13, 2006.

(51) Int. Cl.
*A61B 17/60* (2006.01)
*A61F 2/00* (2006.01)

(52) U.S. Cl.
USPC ............................................................ 606/99

(58) Field of Classification Search
USPC ................. 606/102, 110, 113; 33/542, 543, 33/544, 550, 551, 555.1, 555.4; 73/1.79, 73/1.81; 600/587, 593
See application file for complete search history.

(56) References Cited

U.S. PATENT DOCUMENTS

| | | | |
|---|---|---|---|
| 5,013,318 A | 5/1991 | Spranza, III | |
| 5,041,084 A * | 8/1991 | DeVries et al. | 604/43 |
| 5,201,741 A | 4/1993 | Dulebohn | |
| 5,330,502 A | 7/1994 | Hassler et al. | |
| 5,491,903 A * | 2/1996 | Osborn et al. | 33/555.4 |
| 5,814,098 A * | 9/1998 | Hinnenkamp et al. | 33/512 |
| 5,919,147 A * | 7/1999 | Jain | 600/587 |
| 5,928,239 A | 7/1999 | Mirza | |
| 6,102,930 A | 8/2000 | Simmons, Jr. | |
| 6,110,200 A * | 8/2000 | Hinnenkamp | 623/2.11 |
| 6,440,138 B1 | 8/2002 | Reiley | |
| 6,500,132 B1 | 12/2002 | Li | |
| 6,558,406 B2 * | 5/2003 | Okada | 606/200 |
| 6,652,534 B2 | 11/2003 | Zucherman | |

(Continued)

*Primary Examiner* — Anu Ramana
(74) *Attorney, Agent, or Firm* — Carter, DeLuca, Farrell & Schmidt, LLP

(57) ABSTRACT

A device for dimensioning a circumference of a cavity includes a body with a lumen and a distal aperture. The device also includes a longitudinal member extending through the lumen with a distal end and a proximal end. The longitudinal member is capable of slidable movement through the body between retracted and advanced positions. The device also includes a flexible member adapted to conform to a circumference of a cavity contained, e.g., in an intervertebral disc space. The flexible member is operatively connected to a longitudinal member such that upon retraction of the longitudinal member the flexible member retracts into the lumen. When the longitudinal member is moved toward the advanced position, the flexible member is advanced out of the lumen and expands to conform to a dimension which approximates the circumference of the cavity. An apparatus is provided which includes a device for dimensioning a circumference of a cavity and an access member for facilitating conduction of the device to a surgical site, the device adapted and configured to fit within the access member. A kit is provided which includes a working tube incorporating a vertebral distractor, a spreader for assisting and maintaining the vertebral distractor in a distracted configuration, a closing tube for maintaining the working tube in a closed configuration, and a cavity circumference measuring device.

69 Claims, 20 Drawing Sheets

U.S. PATENT DOCUMENTS

| | | |
|---|---|---|
| 6,679,886 B2 | 1/2004 | Weikel et al. |
| 6,723,058 B2 | 4/2004 | Li |
| 6,983,546 B2 | 1/2006 | Li |
| 2002/0156530 A1 | 10/2002 | Lambrecht et al. |
| 2003/0187457 A1* | 10/2003 | Weber .......................... 606/110 |
| 2006/0036258 A1 | 2/2006 | Zucherman |

* cited by examiner

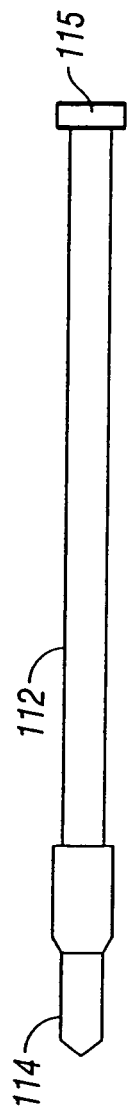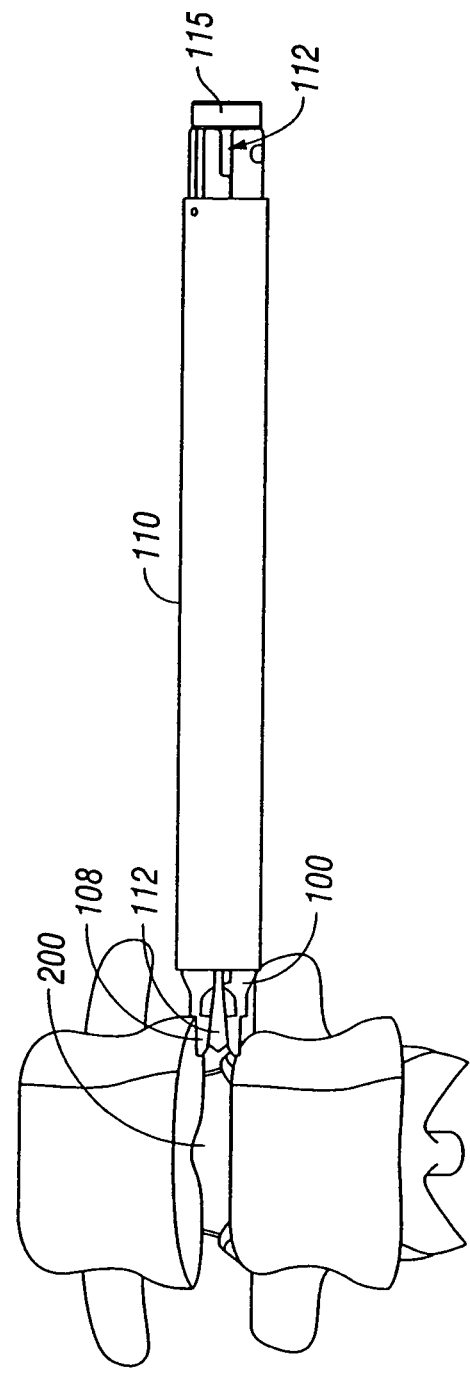
FIG. 7
FIG. 8

APPARATUS FOR DIMENSIONING CIRCUMFERENCE OF CAVITY FOR INTRODUCTION OF A PROSTHETIC IMPLANT

CROSS REFERENCE TO RELATED APPLICATIONS

The present application claims the benefit and priority of provisional application Ser. No. 60/874,618 filed on Dec. 13, 2006 and titled APPARATUS FOR DIMENSIONING CIRCUMFERENCE OF CAVITY FOR INTRODUCTION OF A PROSTHETIC IMPLANT. The entire contents of Ser. No. 60/874,618 are hereby incorporated in its entirety herein.

BACKGROUND

1. Technical Field

The present disclosure is directed to a device for determining a circumference of a cavity such as a spinal disc cavity post nucleotomy. More particularly, the present disclosure is directed to a device for determining whether the cavity is dimensionally sufficient to receive a prosthetic implant.

2. Description of the Related Art

Applications are known in the art which create interior disposed cavities of unknown dimensions associated with herniated discs. A device for determining parameters of blind voids is described in the art. See, e.g., U.S. Pat. No. 6,500,132 B1 to Li (hereinafter "Li").

Although potentially useful, the Li device is deficient. For example, as described therein, the device includes a first flexible element that bulges outwardly to engage interior walls of the void. The device includes a second element that bulges outwardly in a configuration substantially duplicative of the first element bulge, the second element being outside of the void and subject to observation. Although, it may be possible for a surgeon to observe the second flexible element outside the void, the surgeon may also desire to use radiologic imaging to observe the device within the void. However, such imaging using Li's device may be negatively affected by the presence of other elements, e.g., actuator, engagement member, and/or plates, in addition to the first flexible element which obscure the image, i.e., the surgeon may have difficulty distinguishing between the flexible element, the plates, the actuator and the engagement member in determining the size of the blind void.

Additionally, Li's device has a relatively large profile, and a thick width which may prove cumbersome More importantly, the second flexible element would not function within the confines of a narrow cannula since it would be unable to bulge against the side walls of the cannula. If a nucleotomy is being conducted using, inter alia, a cannula, the surgeon would have to remove the cannula before introducing Li's device. The cannula would then be reintroduced for additional spinal procedures, which is inefficient.

Further, depending on the size of the disc space, one or more differently sized prosthetic implants can be introduced into the void during surgery once the void size is determined. Li's device is not well-suited for precisely determining the size the blind void for a pre-dimensioned prosthetic implant in an efficient manner. When using Li's device, the surgeon may visually observe the second flexible element's size. However, to precisely determine the size of the void for the prosthetic implant, the surgeon must measure the second flexible element and then match that measurement to a size of the prosthetic implant. The process may take extra time and requires multiple measurements. It would be advantageous for the surgeon to simply use the device and then automatically know the correct prosthetic implant size.

There is a need in the art for a device for quickly and efficiently determining whether the amount of the nucleus pulposus removed from the intervertebral disc space is sufficient to create a cavity to accommodate a predetermined spinal nucleus implant. Furthermore, there is a need for a device for measuring a cavity that is compact, and has a substantially narrow profile to be quickly introduced into the cavity for measurement through a cannula and then quickly removed from the cannula. There is also a need in the art for a device for measuring a cavity that can be used with imaging techniques and x-ray machines or other scanning devices without cumbersome elements that may obscure the view. There is also a need in the art for a device for measuring the circumferential dimension of a cavity that automatically indicates to the practitioner whether the circumferential dimension is sufficient to accommodate a predetermined implant size. Thereafter, the surgeon can quickly withdraw the instrument through a cannula.

SUMMARY

According to a first embodiment of the present disclosure, there is provided a device for determining sufficiency of a cavity in an intervertebral disc space to receive a spinal nucleus implant of a predetermined dimension. The device has a body forming a lumen with a distal aperture. The device also has a longitudinal member extending through the lumen with a distal end and a proximal end. The longitudinal member is capable of slidable movement through the body. The device also has a flexible looped member operatively attached to the longitudinal member at the distal end. The flexible looped member is capable of going from a contracted configuration to an expanded configuration. The longitudinal member optionally contains one or more markings on a proximal end. In one embodiment, the looped member is radiopaque and configured for radiological imaging.

In one embodiment, the markings on the proximal end portion of the longitudinal member correspond to predetermined circumference amounts of the flexible looped member. In one embodiment, the proximal end portion of the longitudinal member extends past the end of the lumen so the markings can be observed at a suitable distance from the site of the surgical entry.

According to another aspect of the present disclosure, there is provided a device for determining sufficiency of a cavity in an intervertebral disc space to receive a spinal nucleus implant of a predetermined dimension. The device has a body forming a lumen. The body includes a distal opening and a longitudinal member extending through the lumen with a distal end and a proximal end. The longitudinal member is capable of slidable movement through the body. The device also has a deformable member connected to the distal end. The deformable member has an expanded configuration when the deformable member extends outside the lumen and a collapsed configuration when the deformable member is housed in the lumen. In another embodiment, the deformable member is brought into close cooperative alignment with a distal nose outside the lumen in the collapsed configuration.

In the collapsed configuration, the deformable member fits within the confines of the lumen. In one embodiment, the deformable member has a width that is about the same width as the lumen. The deformable member is adjustable to a plurality of different intermediate widths measured across the deformable member when the longitudinal member moves distally. The longitudinal member moves the deformable member relative to the body from the collapsed configuration to the expanded configuration to increase the adjustable width of the deformable member. In one embodiment, the longitudinal member pushes the deformable member out of the lumen and causes the deformable member to expand as it exits the lumen. In one embodiment, the proximal end portion of the longitudinal member contains one or more markings which correspond to predetermined circumference amounts of the deformable member. The proximal end portion of the longitudinal member extends past the end of the lumen so the markings can be observed at a suitable distance from the site of the surgical entry.

In one embodiment, the markings include at least a first marking corresponding to a first prosthetic implant circumference amount. The first prosthetic implant circumference amount corresponds to a first adjustable circumference of the deformable member and is complementary to the first prosthetic implant size so that the first prosthetic implant having the first prosthetic implant size fits in the cavity at that predetermined adjustable width of the deformable member. The markings also include at least a second marking that corresponds to a second prosthetic implant circumference amount different than the first prosthetic implant circumference amount. The second prosthetic implant circumference amount corresponds to a second adjustable circumference of the deformable member and is complementary so that a second differently sized prosthetic implant fits in the cavity at that second adjustable circumference of the deformable member.

According to another embodiment of the present disclosure, there is provided device for dimensioning a circumference of a cavity. The device includes a body forming a lumen having a distal aperture and a longitudinal member extending through the lumen with a distal end and a proximal end. The longitudinal member is capable of slidable movement through the body between retracted and advanced positions. The device also has a flexible member adapted to conform to a circumference of an intervertebral disc space. The flexible member is operatively connected to the longitudinal member such that upon retraction of the longitudinal member, the flexible member retracts into the lumen. When the longitudinal member is moved toward the advanced position the flexible member is advanced out of the lumen and expands to conform to a dimension which is limited by and approximates the circumference of the intervertebral disc space. The device also has the longitudinal member with a proximal end with at least one marking. The marking corresponds to a predetermined circumference of a prosthetic implant. When the longitudinal member is advanced from the retracted configuration to the expanded configuration, a flexible member circumference expands to contact a lateral side wall of the cavity. The flexible member circumference upon contacting the lateral side wall of the cavity may correspond to the marking on the proximal end of the longitudinal member. The marking corresponds to the predetermined prosthetic implant circumference when the predetermined prosthetic implant is at its maximum diameter, e.g., when hydrated. Visualization of the marking indicates that the circumferential dimension of the cavity is sufficient to accommodate the circumferential dimension of the prosthetic implant and thus provide a proper fit within the cavity.

According to another embodiment of the invention, a device for dimensioning a circumference of a cavity adapted to fit within the confines of an access member in combination with an access member is provided. The device includes i) a tubular body adapted and configured to fit within an access member, said tubular body having a lumen extending therethrough, the tubular body having distal and proximate ends, ii) a longitudinal member slidably disposed within the lumen, the longitudinal member having distal and proximate end portions, iii) a deformable member operatively attached to the distal portion of the longitudinal member, the deformable member adapted to fit within said lumen when drawn into said lumen by said longitudinal member and further adapted to expand into an expanded configuration when pushed out of said lumen by said longitudinal member, said expanded configuration corresponding to an approximation of the circumference of a cavity. In one embodiment, the cavity is a cavity formed in a spinal disc space by removal of all or a portion of the nucleus pulposus. In one embodiment, the proximate end portion of said longitudinal member contains one or more markings which respectively correspond to predetermined circumference amounts of the deformable member, said proximal end portion adapted to extend out past the proximal end of said tubular body such that said one or more markings are visible outside said tubular body. In one embodiment, said proximate end portion further includes a handle for grasping and slidably manipulating said longitudinal member. The access member provides access to a surgical site and has a tubular shape which is adapted to receive the device and allow it to be conducted to the surgical site. Examples of access members are cannulas, trocars and distractors which include portions which approximate to form a tubular member having a lumen extending through its length.

According to another embodiment of the present disclosure, there is provided a kit for use in implanting a prosthetic implant. The kit includes an access member referred to herein as a working tube. The working tube has a first member and a second member which are pivotally attached to each other. In one embodiment, the first and second members are pivotally attached to one another by a first pivot and a second pivot. The first member and second member have first and second respective distraction ends which cooperate by virtue of the pivotal attachment to form a vertebral distractor. The first member is brought into approximation with the second member for distracting a disc space at the distraction end. The first member and the second member form a lumen therebetween when brought into approximation. The kit also includes a spreader configured to be inserted into the lumen. The spreader has a distal end configured to assist in maintaining the distracted disc space. The kit further includes a closing tube configured to be introduced in coaxial alignment over the working tube. The closing tube prevents the opening of the working tube and confines movement of the first member and the second member to the approximated position. The spreader may be removed when the closing tube is disposed in coaxial alignment with the working tube.

The kit also includes a cavity circumference measuring device adapted and configured to fit within the confines of the lumen formed by approximation of the first and second members of the working tube. The measuring device includes a tubular member which is adapted and configured to slidably receive a longitudinal member having a flexible member disposed at one end thereof. The flexible member is adapted to conform to a circumference of the intervertebral disc space. The flexible member is operatively connected to the longitudinal member at one end such that upon retraction of the longitudinal member the flexible member retracts at least partially into the tubular member. When the longitudinal member is moved toward an advanced position, the flexible member is advanced out of the tubular member and expands to conform to a dimension which approximates the circumference of the intervertebral disc space. One or more circumference indicating marks on the longitudinal member are visible to the operator of the cavity circumference measuring device, said marks corresponding to predetermined circumference amounts of the flexible member, to inform the operator of the circumferential size of the cavity and automatically indicate which pre-sized implant is of suitable size for implantation. The pre-sized implant is inserted into the disc space.

BRIEF DESCRIPTION OF THE DRAWINGS

The above and other aspects, features, and advantages of the present disclosure will become more apparent in light of the following detailed description when taken in conjunction with the accompanying drawings in which:

FIG. 7 is side view of a spreader for assisting and supporting the distractor function of the access member illustrated in FIG. 6.

FIG. 8 is a side view illustrating the working tube with a closing tube over the working tube with the spreader illustrated in FIG. 7 in the lumen of the working tube to maintain the working tube in the distracted configuration at the surgical site;

DETAILED DESCRIPTION

Figure 1:
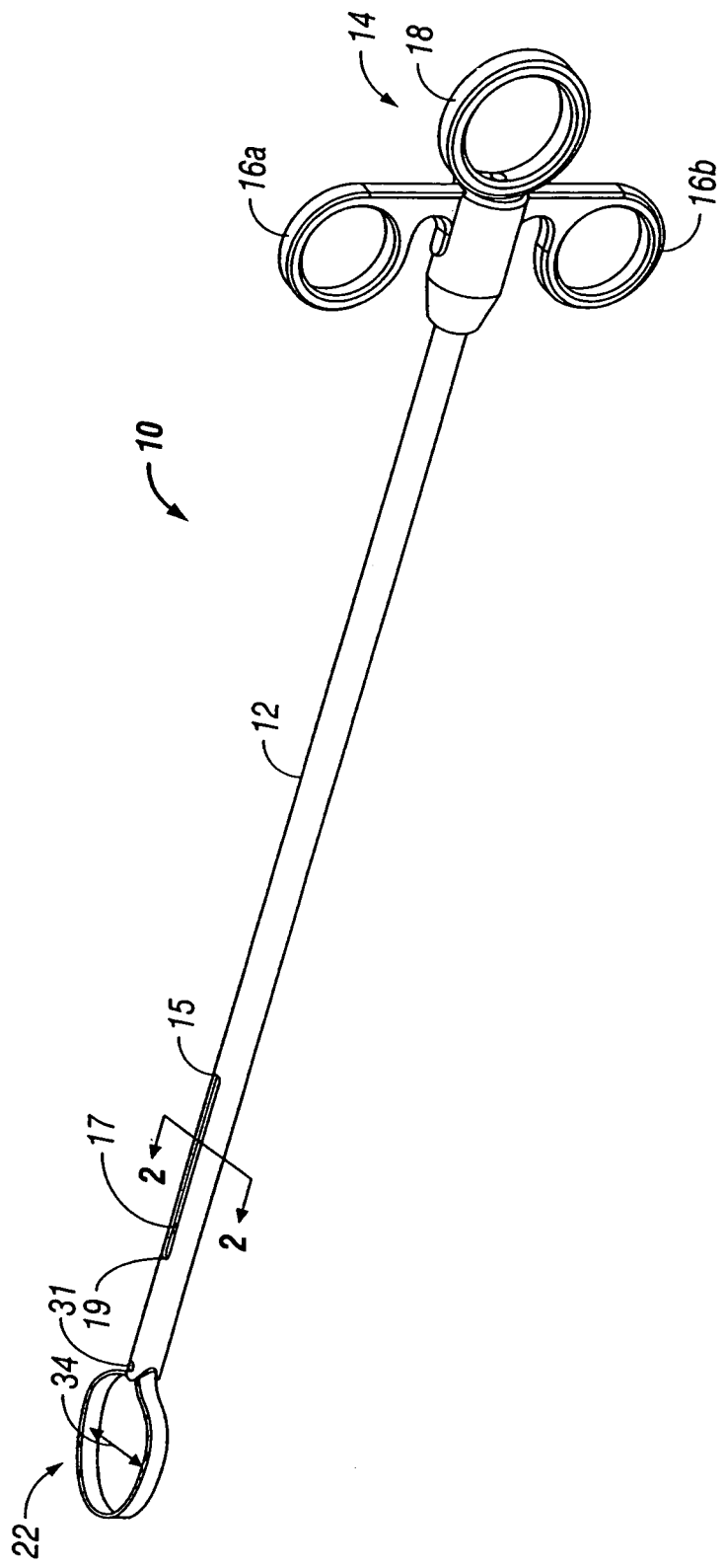
FIG. 1 is a perspective view of a device for determining a sufficiency of a cavity in an intervertebral disc space to receive a spinal nucleus implant of predetermined dimension.

Embodiments of the presently disclosed device will be described herein below with reference to the accompanying drawing figures wherein like reference numerals identify similar or identical elements. In the following description, well-known functions or constructions are not described in detail to avoid obscuring the disclosure in unnecessary detail. It should be understood that, as used herein, the terms "circumference" and "circumferential" are used in their customary manner, e.g., referring to the boundary of a circle, but are also intended to encompass ellipsoid and rectangular configurations which may have regular or irregular topography. This broad reading of the terms "circumference" and "circumferential" is meant to take into account the fact that cavities which result from cavitation procedures or natural processes can have irregular shapes. The circumference of such cavities can be measured in accordance with the present disclosure.

Referring now to FIG. 1, there is shown a perspective view of the device 10. The device 10 advantageously determines sufficiency of a cavity in an intervertebral disc space to receive a spinal nucleus implant of a predetermined circumferential dimension with the nucleus pulposus fully or partially removed. In operation, a distal end of the device 10 is inserted into the cavity for treatment purposes. The treatment may be the treatment of a herniated disc, or treatment of degenerative spinal disc disease without spinal fusion.

The device 10 may be used, e.g., with techniques to treat disc disease whereby a degenerated nucleus pulposus is replaced, in whole or in part, with a prosthetic implant instead of spinal fusion. The prosthetic implant restores disc function to the spine in a minimally invasive surgical technique. In one embodiment, different sized prosthetic implants may be used depending on the size of the disc space, the amount of the degenerated nucleus pulposus that is removed and the size of the annulus such as shown by way of example in FIG. 12. In one embodiment, the prosthetic implant may be introduced in a dry or xerogel state. The implant is inserted into the excised disc space, and then once properly positioned in the cavity, water, body fluid, or another suitable liquid flows into or is introduced into the cavity to hydrate the prosthetic implant and to increase a size of the prosthetic implant. In this embodiment, the prosthetic implant may have a number of different dry width sizes or circumferences. Each dry prosthetic implant may have a second hydrated width size that will correspond to the amount of the degenerated nucleus pulposus that is removed to provide support to the diseased or herniated disc.

FIG. 1 shows the device 10 that has a longitudinal body 12 and an actuator portion 14. The device 10 determines sufficiency of a cavity in an intervertebral disc space to receive a spinal nucleus implant of a predetermined dimension. The longitudinal body 12 has a lumen (FIG. 2) formed therethrough. The longitudinal body 12 is a resilient member and is connected to a portion of the actuator 14 at the proximal end. In one embodiment, the longitudinal body 12 is a resilient metallic member such a nickel, titanium or stainless steel. However, in another embodiment, the longitudinal body 12 can be any surgically acceptable resilient plastic material, e.g., a biocompatible thermoplastic material such as polyethylene and the like. The portion of the actuator 14 which is connected to the longitudinal body has a pair of finger loops 16a, 16b for helping grasp the device 10. The actuator portion 14 also includes a loop member 18. The loop member 18 is connected to a push rod 20 that is disposed through the lumen of the body 12 in concentric fashion, and the push rod 20 is intended to slide through the longitudinal body 12. The loop member 18 may be moved proximally and distally to move the push rod 20 through the longitudinal body 12. The actuator 14 is shown as having the loop member 18 and a pair of finger loops 16a, 16b, however other handle configurations are envisioned and the arrangement shown is not limiting.

The device 10 also has an end effector 22. The end effector 22 is a flexible looped member that is inserted into a cavity disposed within an intervertebral disc space to determine whether the circumference of the cavity can receive a spinal nucleus implant of a predetermined circumferential dimension. The end effector or flexible member 22 preferably can be manipulated distally and proximally by the push rod 20. In one aspect, the end effector 22 can be withdrawn entirely into the device 10, or in another aspect the end effector 22 can be extended completely out of the device 10 and in yet another aspect the end effector 22 can be manipulated at various intermediate positions therebetween. The end effector 22 preferably is sufficiently flexible so as to adjust a width 34 measured across the lateral sides or diameter (if the end effector 22 is circular) as shown in FIG. 1 by manipulating the push rod via the loop member 18. The end effector 22 is flexible and can be manipulated from a negligible or zero width when the end effector 22 is completely in the body 12 to a maximum width or circumference when the end effector 22 is completely advanced outside of the body 12 and adjustable to any other intermediate width therebetween to approximate a cavity. The body 12 has a window 15 on a lateral side. The push rod 20 has a pin 17 that will engage a lateral edge 19 of the window 15 to limit distal movement of the end effector 22.

Figure 2:
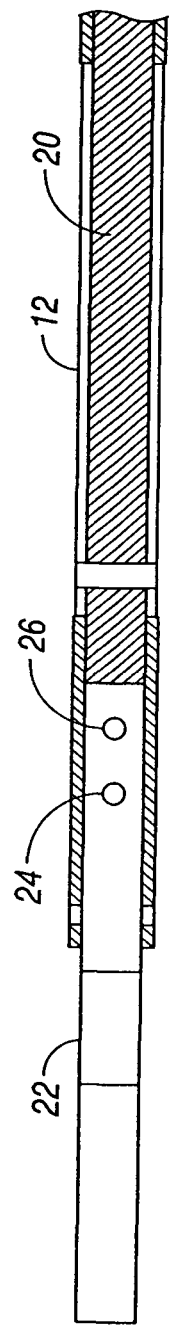
FIG. 2 is a cross sectional view of the device along line 2-2 of FIG. 1 showing an end effector connected to a push rod.

Referring now to FIG. 2, there is shown a cross sectional view of the end effector 22 connected to the push rod 20 that is disposed in the body 12. As can be understood from the figure, the push rod 20 shown in cross sectional view along line 2-2 of FIG. 1 and is shown in cross hatching for illustration purposes. The push rod 20 is connected to the end effector 22 by a first pin 24 and a second pin 26. Although shown as being connected by pins 24, 26, it is contemplated that the end effector 22 may be connected to the push rod 20 by other means including welding, adhesive, direct connection, ultrasonic welding or the end effector 22 may be die cast as one integral piece with the push rod 20. Various configurations are possible and within the scope of the present disclosure and the operative connection is suitable such that the end effector 22 may be moved proximally and distally by the push rod 20 with ease and in a repeated manner.

Figure 3:
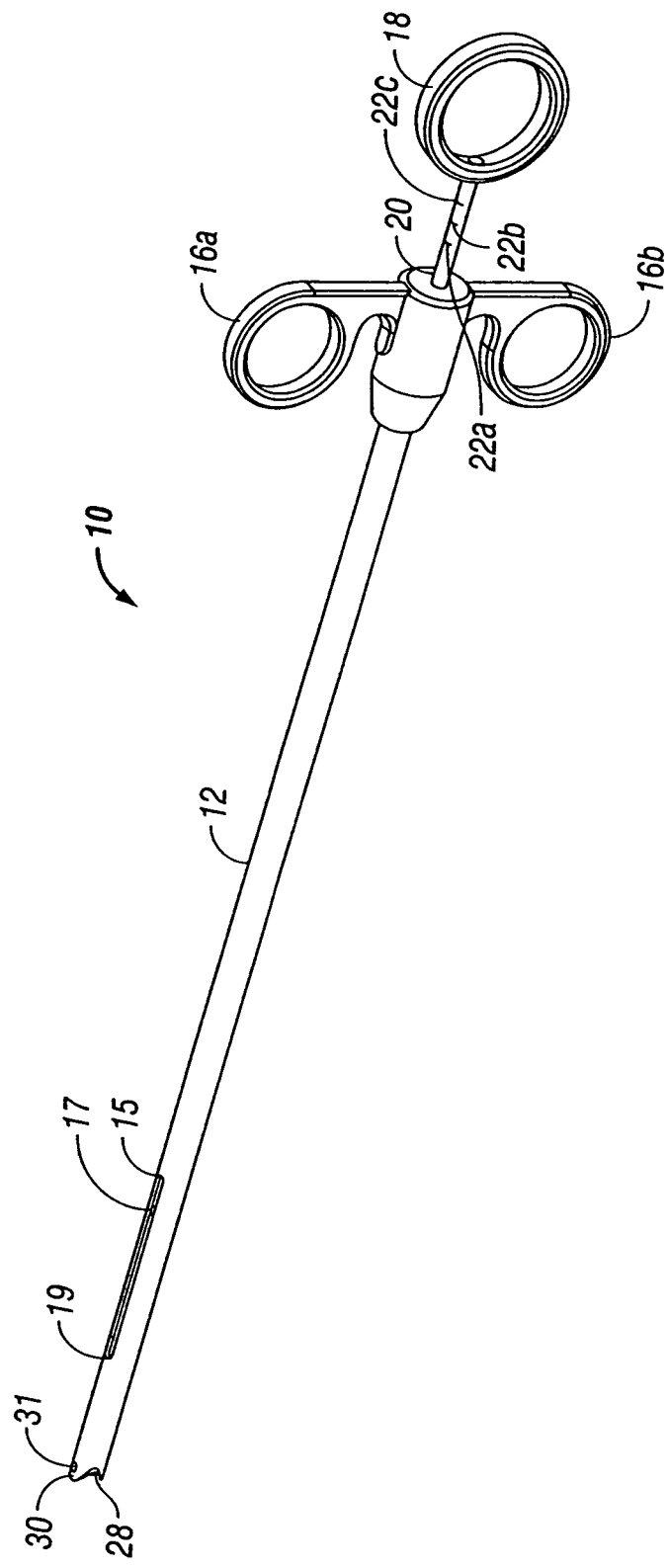
FIG. 3 is another perspective view of the device of FIG. 1 with the end effector withdrawn into the body of the device.

Referring to FIG. 3, there is shown the device 10 in a retracted or collapsed configuration with the end effector (not shown) of the device 10 being withdrawn or completely in the body 12 of the device 10 through the aperture 28 formed in the distal end 30 of the body 12. In this aspect, the end effector has a substantially zero or negligible width. The device 10 can be arranged in the retracted configuration simply by pulling the looped handle 18 in a proximal direction as shown. This proximal movement causes the push rod 20 to be retracted in a proximal manner which also moves the end effector 22 in the proximal manner. In this manner, the end effector 22 does not extend out the aperture 28, and the device 10 has a slim profile that is advantageous for manipulating the device 10 in a spinal surgical environment in a quick and easy manner such as through an access member such as a tube, a cannula or trocar. In this manner, the end effector 22 does not impede or increase a width or length of the device 10 and the device 10 can be manipulated in a compact and advantageous manner.

Figure 4:
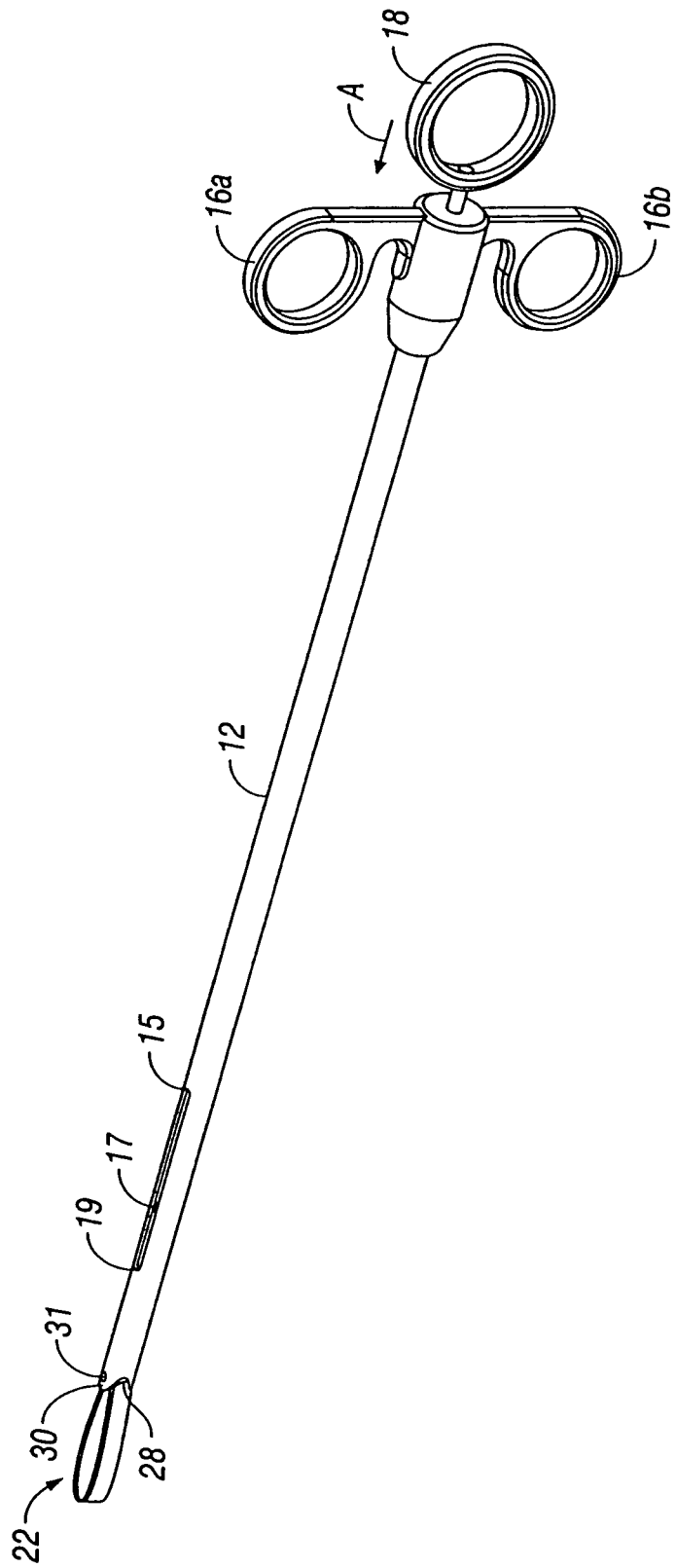
FIG. 4 is a another perspective view of the device of FIG. 1 with the end effector partially extended from the body of the device.

Referring now to FIG. 4, there is shown the device 10 in an expanded configuration with the end effector 22 of the device 10 partially expanded out of the body 12 of the device 10 and through the aperture 28 formed in the distal end 30 of the body 12. The device 10 can be arranged in the expanded configuration simply by moving the looped handle 18 in a distal direction as shown by arrow A. This distal movement causes the push rod 20 to be advanced in a distal manner which also moves the end effector 22 in the distal manner.

In this manner, the end effector 22 extends out the aperture 28 where it circumferentially expands. When utilizing an access member such as a cannula, the distal end 30 of the device 10 extends past the end of the access member and is introduced into the cavity or in proximity to the cavity for approximation of the cavity. In this manner, the end effector 22 increases its circumference to approximate the circumference of the cavity within the disc space to determine the sufficiency of the cavity, i.e., to determine whether the circumference of the cavity is sufficient to receive a spinal nucleus implant of a predetermined circumferential dimension. The device 10 determines a dimension of the cavity when the end effector 22 contacts the lateral side walls of the cavity and can no longer expand without exertion of extraordinary pressure. Extraordinary pressure would cause the end effector 22 to deform, e.g., bow inwardly and away from the lateral side walls. In normal operation, however, when the end effector stops expanding, the push rod 20 and loop handle 18 are prevented from moving distally, and the surgeon will feel resistance. In one aspect, the dimension may be a length of the cavity. In another aspect, the dimension may be a width of the cavity. In yet a further aspect, the dimension may be a width and the length of the cavity or a circumference of the cavity. Preferably, the end effector 22 measures a "foot print" or a specific known predetermined circumference of a specific prosthetic implant that is desired to be introduced into the cavity to determine whether the specific prosthetic implant will fit into the cavity. In one embodiment, the end effector 22 is flexible enough to generally correspond to the circumference topography of the excised disc space when the end effector 22 is deployed in the cavity.

Figure 5:
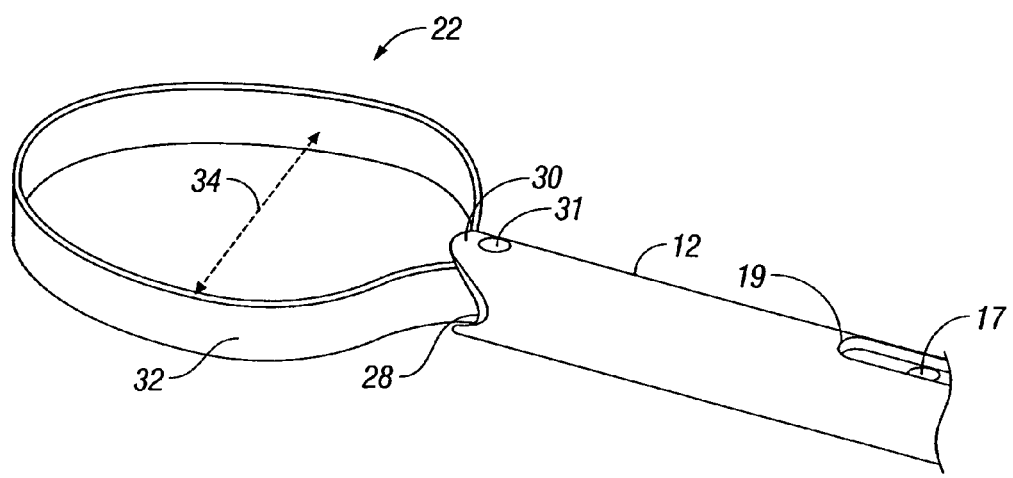
FIG. 5 is a close up view of the end effector of FIG. 4 in a relatively more extended and expanded configuration.

Referring now to FIG. 5, there is shown a close up view of the distal end 30 of the body 12. The end effector 22 extends from the body 12 through aperture 28 in the distal end 30. The end effector 22 is made from a flexible element such as a metal strip or a flexible polymeric material. In one aspect, shape memory alloys are particularly advantageous for such a material; e.g., nitinol (NiTi), CuZnAl, CuAlNi, and the like. Preferably, in each embodiment, the end effector 22 is made from a biocompatible material that can be used once and discarded. Alternatively, the device 10 with the end effector 22 can be reusable and can be sterilized for later use. Various configurations are possible and within the scope of the present disclosure.

In one embodiment, the end effector 22 is made from a metal. It is envisioned that the end effector 22 can be made from nitinol, nickel/titanium material or alloy that is biocompatible. When fully deployed, the end effector 22 preferably has a substantially "O", circular or elliptical shape and is operatively connected to the push rod 20 as discussed above, and has a sufficient width or thickness so the end effector 22 will not bend back on itself once contacting the lateral side walls of the cavity in the absence of extraordinary force. It is envisioned that the end effector 22 in one embodiment is made from a metal ribbon, however in another embodiment; the end effector 22 may be made from a biocompatible polymer, e.g., a thermoplastic polymer. Other configurations of the end effector are suitable, e.g., a wire such as an elastic wire, a cable, a braided cable, a rope or a tape. Various configurations are possible and within the scope of the present disclosure. The end effector 22 may be made from any material that can assume a first shape and be sufficiently flexible and deformable to be withdrawn into the body 12 of the device 10. The end effector 22 has a lateral side 32, and a thickness. The thickness is preferably about 0.1 mm to about 0.25 mm. It should be understood, however, that one skilled in the art can vary the thickness to other values depending, e.g., on the material, the length of the end effector and the intended surgical environment.

In one embodiment, the proximal end of the push rod 20 has a plurality of markings 22a, 22b, and 22c (FIGS. 3, 9, 9A and 9B). In this embodiment, only three markings 22a, 22b, and 22c are shown simply for illustration purposes; however it should be appreciated that the push rod 20 may have any number of markings or indicia to assist with the surgical spinal procedure. The push rod 20 may have length, width, or depth gradations to measure the cavity or one more dimensions of the cavity such as the sufficiency of the cavity in the intervertebral disc space to receive a spinal nucleus implant of a predetermined dimension. It is envisioned that the push rod 20 may have several different types of marking to measure several parameters simultaneously. Various configurations are possible and within the present disclosure.

In this embodiment, the push rod 20 has markings 22a, 22b, and 22c that correspond specifically to a first prosthetic implant width size, a second prosthetic implant width size, and a third prosthetic implant width size. The markings 22a, 22b, and 22c preferably indicate the circumference of the cavity and the sufficiency of the cavity in the intervertebral disc space to receive a spinal nucleus implant of a predetermined dimension. In particular, when the end effector 22 can no longer expand due to the resistance exerted by the walls of the cavity, the push rod will stop advancing. The surgeon can then observe the position of the push rod 20 and note where each specific marking 22a, 22b, and 22c is relative to the the proximal end of the longitudinal tube 12 and then immediately know the size of the circumference of the cavity and which size specific prosthetic implant will best fit within the cavity. Since the markings are observable at a remote location outside the cavity or access member, the device 10 allows this measurement to be determined without having to look at the end effector 22 in the cavity, which cannot be seen by the surgeon. It is envisioned that the specific markings 22a, 22b, 22c may correspond to a size of the implant by a general category such as "A", "B", "C", and "D" sized implants, or the markings may show the exact size of the implant in units. Various configurations are possible and the present disclosure is not limited to any specific marking arrangement.

The surgeon may introduce the distal end of the device 10 into the cavity in the retracted or collapsed configuration or where the end effector 22 is disposed in the body 12 of the device 10 as shown. Using the actuator 14, the surgeon can then carefully move the end effector 22 from the collapsed configuration to the expanded configuration thereby causing the diameter 34 of the end effector 22 to increase or decrease to approximate the cavity and determine which marking 22a, 22b, and 22c is visible on the push rod 20.

FIG. 5 illustrates that the distal end 30 has a pin 31. Pin 31 extends perpendicularly through a lumen (not shown) of the longitudinal body 12 at the distal end 30. Pin 31 assists with spreading the end effector 22 from the collapsed configuration and into the expanded configuration shown in FIG. 5. In FIG. 5, the pin 31 is seated between the two sides of the end effector 22. In this manner, the end effector 22 can quickly move between expanded and contracted configurations so the surgeon can efficiently use the device. In addition, the pin 31 serves as a stop which prevents the end effector 22 from being drawn too far within the device.

Figure 6:
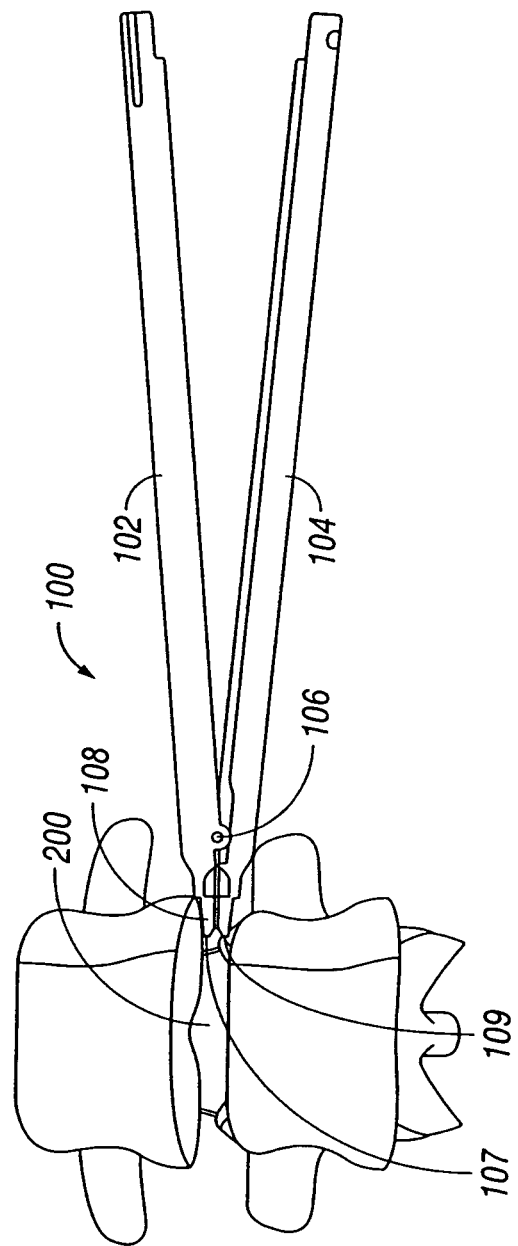
FIG. 6 is a schematic illustration of an access member which functions as a distractor for distraction of adjacent vertebrae and which is capable of forming a working tube having a lumen to introduce the device for determining a sufficiency of a cavity to a surgical site.

FIGS. 6 through 12 illustrate the device 10 and other instruments which may be utilized in operation in a surgical environment. Referring now to FIG. 6, there is shown an access member in the form of a working tube 100 having a first member 102 and a second member 104. The working tube 100 is made from a biocompatible material such as titanium, or stainless steel, or a resilient polymer such as polyethylene or polyethylene terephthalate. The working tube 100 is placed in a predetermined location or between vertebrae as shown in proximity to a cavity 200 in the disc space. For purposes of clarity, the annulus of the spinal disc is not shown in the drawings. It should be understood that the cavity 200 in the disc space resides within the bounds of the annulus and may or may not encompass the entire disc space. The cavity may be created artificially, e.g., by any denuculeation procedures known in the art, or by a natural disease process. Accordingly, the cavity 200 may only encompass a portion of the entire disc space or it may substantially encompass the entire disc space. The working tube 100 preferably assists with the introduction of the distal end 30 of the device 10 into the cavity 200 where the surgical conditions require disc space distraction.

In certain instances, the disc space may be collapsed or partially collapsed and may require a disc space distraction. The working tube 100 preferably assists with the disc space distraction and increases the distance between vertebrae using a lever type action. The first and the second members 102, 104 are connected by a pivot 106 near a distal end 107 which is near or in proximity to the cavity 200. The first and the second members 102, 104 preferably are intended to be used in connection with a collapsed disc space to distract the disc space. First member 102 has a jaw 108 at its distal end. Second member 104 has a jaw 109 at its distal end. A first distraction pin and a second opposite distraction pin (not shown) are disposed on the opposite sides of the pivot 106 to permit the first member 102 to pivot in relation to the second member 104 without blocking any interior space therebetween which is used to form a lumen to introduce the distal end 30 of the device 10 into the disc space 200. The jaws 108 and 109 of the first member 102 and the second member 104 are inserted into an opening or surgical incision and are positioned in proximity to the collapsed disc space for disc space distraction. The distraction also may be aided by aligning the patient in a bent manner over a surgical table to further assist with distraction of the intervertebral disc space. The first member 102 and the second member 104 are brought into approximation with one another to push the jaws 108 and 109 apart and act as a lever to push apart adjacent vertebrae and raise a collapsed disc space at the distal end 107. In one embodiment, the collapsed disc space that is raised may include a distraction distance of about 4.7 mm to 8.4 mm.

Referring now to FIG. 8, a closing tube 110 is shown concentrically disposed over first and second members 102 and 104 after the members 102 and 104 have been brought into approximation and jaws 108 and 109 distract the adjacent vertebrae. The closing tube 110 prevents the first and second members 102 and 104 from spreading apart, thus maintaining the jaws 108 and 109 in spaced apart relation. The closing tube 110 is preferably shorter than the working tube 100 to allow access to the proximal end of the working tube and to avoid interfering with the distal end 107 of the working tube 100. A spreader 112 is shown in FIG. 7 which can be used to assist and support the spreading action of the jaws 108 and 109. The distal end 114 of the spreader 112 is configured to exert cam pressure against the jaws 108 and 109 and abut the interior of the distal end of the working tube 100 to help counter any opposing force exerted by the distracted vertebrae. A disc-shaped handle 115 is located at the proximal end of the spreader 112. The handle 115 aids in grasping the spreader 112 and has a diameter which is preferably equal to or greater than the outside diameter of the working tube 100. In this manner, the handle prevents the spreader 112 from being completely inserted into the lumen 116 formed in the working tube 100 when first and second members 102 and 104 are brought into approximation. The distal and proximal ends of the spreader are shown disposed in the lumen created by approximation of members 102 and 104 in FIG. 8.

Figure 8A:
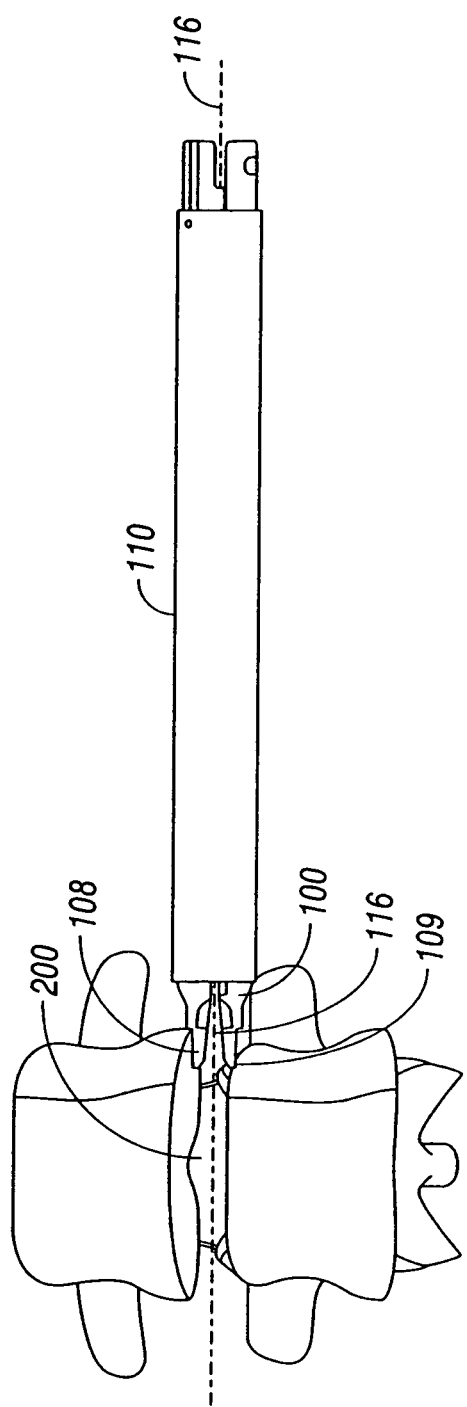
FIG. 8A is a side view of the closing tube and the working tube having the spreader removed.

Referring now to FIGS. 8 and 8A, the working tube 100 is closed and the spreader 112 (FIG. 7) is placed through the working tube 100 to support the working tube 100 at its distal end 107. The spreader 112 may be brought through the working tube 100 to the distal end 107. The distal end of the spreader 114 is introduced into the lumen 116 and the distal end of the spreader 114 helps maintains the distraction space that is formed by the working tube 100 as discussed above. Alternatively, the spreader 112 is placed between members 102 and 104 before they are brought into approximation, and then the members 102 and 104 are brought into approximation around the spreader.

Thereafter, the closing tube 110 is placed over the first working tube 100 to keep the first working tube 100 closed, and prevent the first member 102 and the second member 104 from moving opposite one another as shown in FIG. 6. The closing tube 110 has a unitary cylindrical configuration and is placed over the working tube 100. The closing tube 110 placed over the first working tube 100 keeps the distraction distance fixed as the first working tube 100 abuts the interior space of the closing tube 110 and cannot move to the opened position. As shown in FIG. 8, once the position of the jaws and distraction space is maintained by the closing tube 110, the spreader 112 can be withdrawn from the lumen 116. The spreader 112 is then removed and the lumen 116 is formed within the first working tube 100 and the closing tube 110 (See FIG. 8A). The lumen 116 provides access to the operative site and access to the distracted space. An optional nut (not shown) may be threaded to the proximal end of the closing tube 110. This ensures that the closing tube 110 remains connected and closed over the working tube 100 to maintain the distraction disc space.

Figure 9:
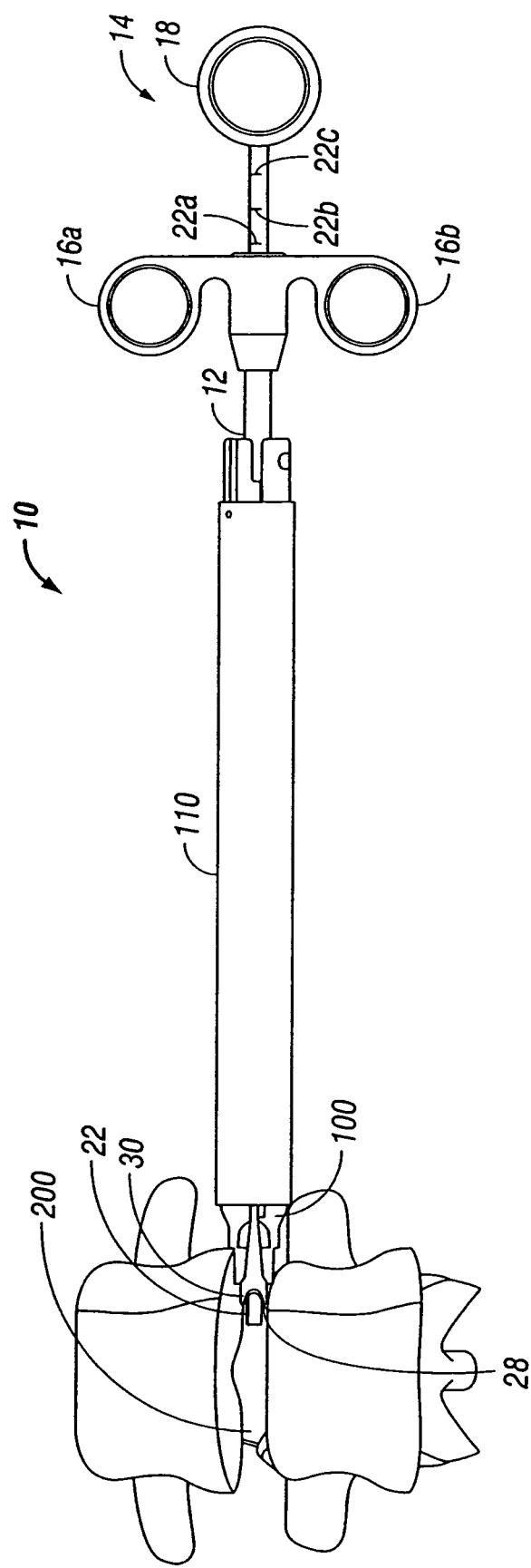
FIG. 9 is side view illustrating the device for determining a sufficiency of a cavity introduced through the lumen formed by the working tube and closing tube of FIG. 8A with the end effector partially extended in the spinal disc space.

Referring now to FIG. 9, there is shown the device 10 with the distal end 30 of the device 10 introduced through the lumen 116 formed by the working tube 100 and the closing tube 110. The lumen 116 provides access to cavity 200. As can be understood, the body 12 of the device 10 is introduced through the lumen 116, and once the distal end 30 of the body 12 reaches the operative site or cavity 200, the end effector 22 can be introduced into the cavity 200 from inside the body 12. In other words, the end effector 22, once introduced in the cavity 200, is manipulated from the collapsed configuration to the expanded configuration. This is advantageous since, the end effector 22 has a substantially zero width in the retracted position and can travel distally through the lumen 116 formed by tubes 100, 110 with ease.

Figure 9A:
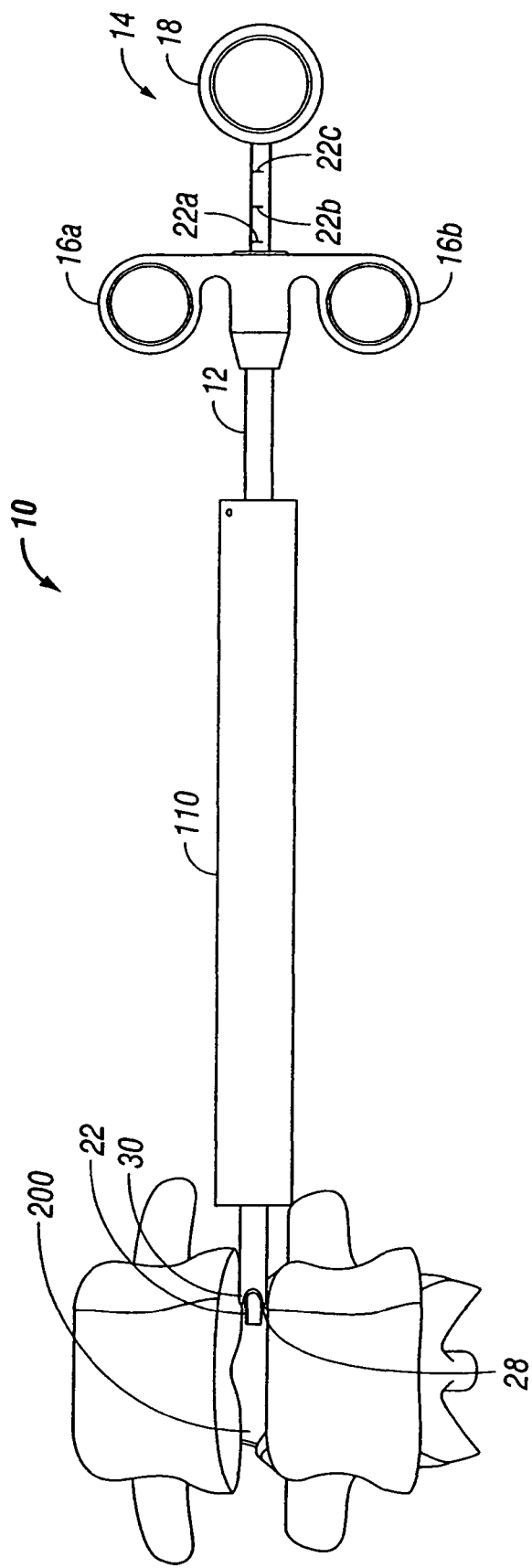
FIG. 9A is schematic illustration of the device for determining a sufficiency of a cavity inserted into an access member in the form of a cannula to access a surgical site instead of the working tube and the closing tube.
Figure 9B:
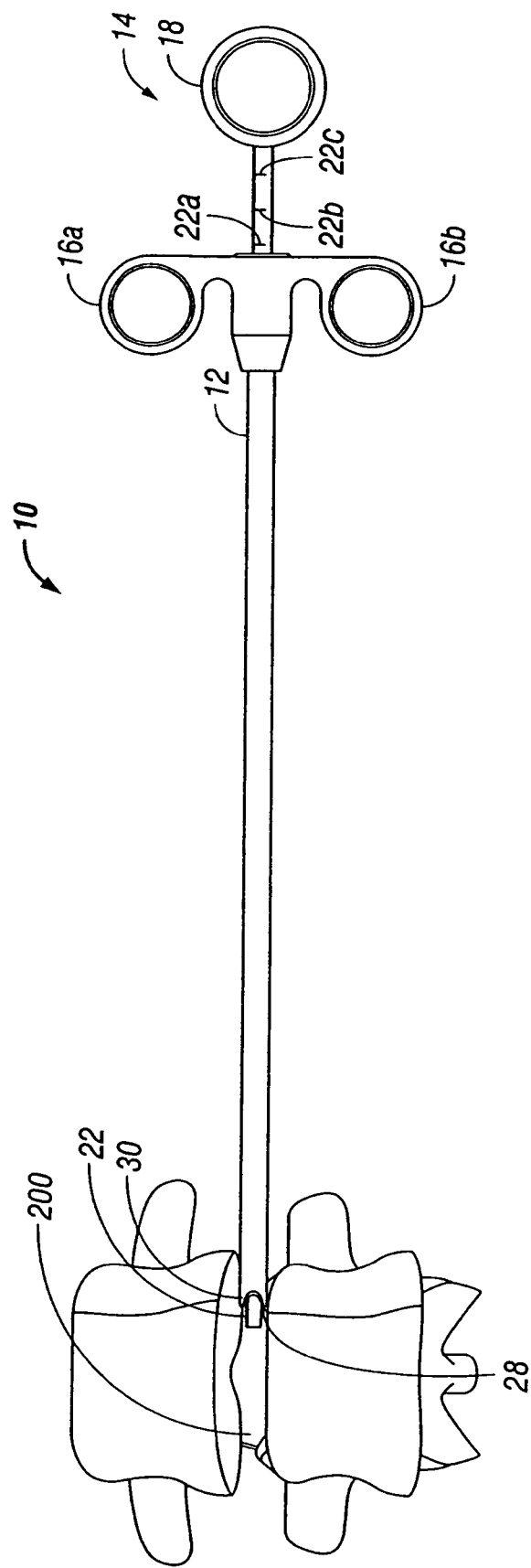
FIG. 9B is a side view of the device with the end effector introduced into the spinal disc space without an access member.

It should be appreciated that the device 10 may be used with any access device such as a plain cannula 110' as shown in FIG. 9A or may be used where no cannula 110' or tubes 100, 110 are present, and where the end effector 22 of the device 10 is directly inserted into the cavity 200 as shown in FIG. 9B. Various configurations and surgical environments are contemplated and within the scope of the present disclosure. It should be appreciated that the device 10 may be used in a number of different spinal surgical procedures for disc replacement and a number of different approaches to the spinal disc cavity. These approaches include a posterior disc approach, and anterior disc approach, a lateral approach, or an anterolateral transpsoatic approach.

Figure 10:
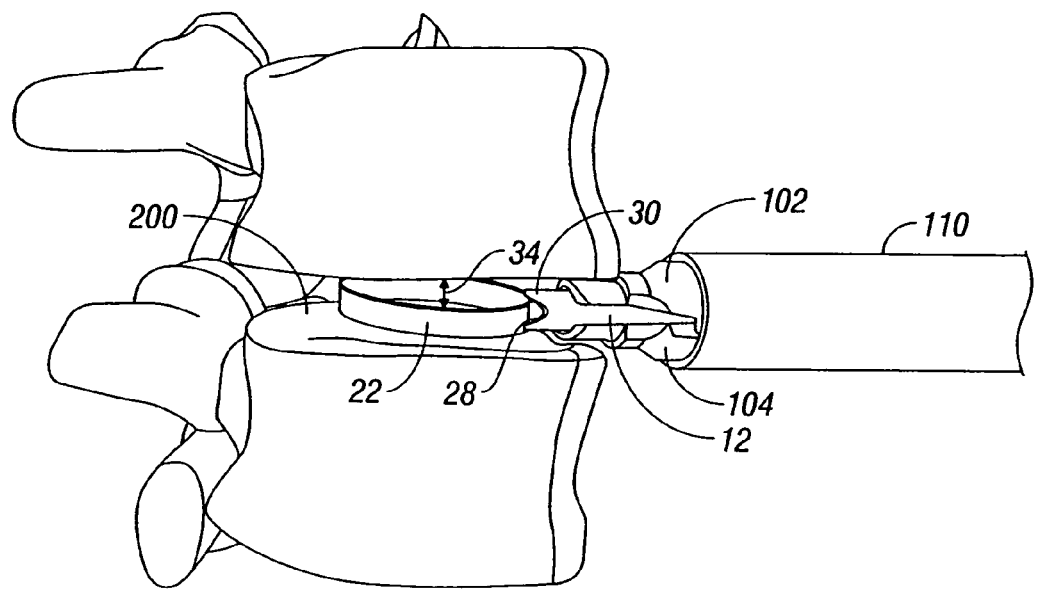
FIG. 10 is an enlarged side view of the end effector in an advanced position and disposed in the spinal disc space for measuring the circumference of a cavity therein.

FIG. 10 illustrates a close up view of the end effector 22 in the cavity 200. As can be seen, the end effector 22 is introduced through the distal opening 30 and through aperture 28 to measure one or more dimensions of the cavity 200. In one embodiment, the end effector 22 may measure whether enough tissue of the nucleus pulposus has been removed by a cavitation procedure such as a nucleotomy or discectomy to approximate the cavity 200 and to determine a sufficiency of the cavity 200 to receive a spinal nucleus implant of a predetermined dimension.

Figure 11:
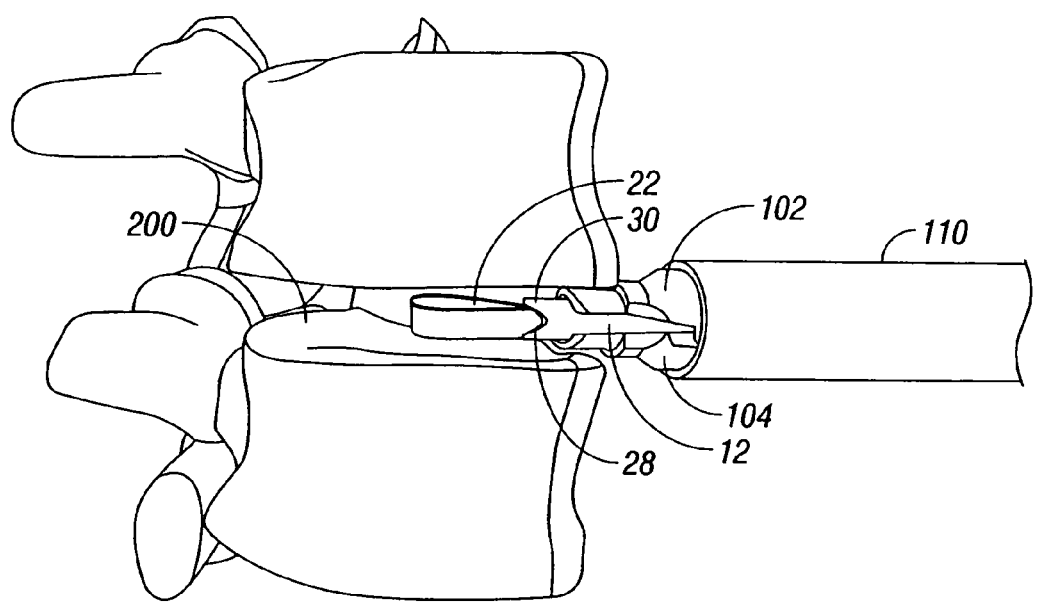
FIG. 11 is an enlarged side view of the end effector in a partially retracted position in the intervertebral disc space.

It is advantageous since the end effector 22 may be withdrawn into the body 12 of the device 10 so the device 10 can be inserted through the lumen 116 of the tube 100 for ease of entry to the cavity 200. In this manner, the end effector diameter 34 is reduced. Thereafter, as shown in FIGS. 10 and 11, the end effector 22 can be adjusted to increase its width/circumference and contact either the lateral side walls of the cavity 200 or the amount of the nucleus pulposus that remains in the cavity 200. Referring again to FIG. 9, the surgeon using the device 10 can then determine a sufficiency of a cavity in an intervertebral disc space to receive a spinal nucleus implant of a predetermined dimension and whether a specific prosthetic implant having a predetermined circumference will fit into the cavity 200. The surgeon will then manipulate the looped handle 18 to manipulate the end effector 22 in the cavity 200 so the end effector 22 contacts the lateral side walls of the cavity 200 to approximate the cavity 200. Once the surgeon cannot manipulate the looped member 18 distally and the end effector 22 is contacting the lateral side walls of the cavity 200, the surgeon can optionally confirm this condition by taking a radiological image. The surgeon can observe the markings 22a, 22b, 22c at the proximal end of the device 10 outside the cavity 200 on the push rod 20. The surgeon can determine which marking 22a, 22b, 22c is visible on the push rod 20 at the approximated circumference of the end effector 22 to determine a circumference of the cavity and a sufficiency of a cavity to receive a spinal nucleus implant of a predetermined dimension. In one embodiment, alignment of a marking with the distal end of the tube 12 signifies that the circumference of the end effector 22 matches the value defined by the marking.

In yet another embodiment, the prosthetic implant may be a dried prosthetic implant that has a first size when dry and a second larger size when hydrated. The markings 22a, 22b, 22c on the push rod 20 may correspond to a hydrated size of the dried prosthetic implant so the surgeon can easily determine and fit the correct prosthetic implant into the cavity 200. It is appreciated that the device 10 is useful since the hydrated size of the prosthetic implant may not be readily appreciated when observing the dry prosthetic implant. Thus, the markings 22a, 22b, and 22c on the push rod 20 that correspond to the hydrated sizes of the prosthetic implant assists the surgeon with approximating the cavity 200.

Figure 12:
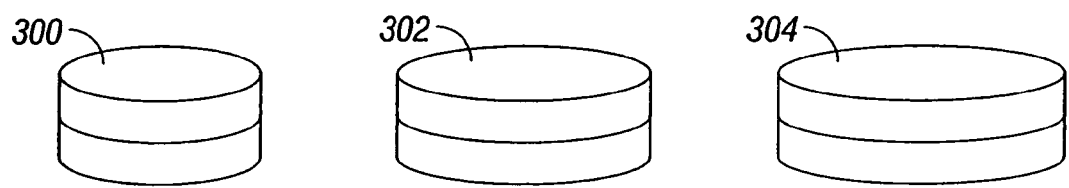
FIG. 12 shows a number of prosthetic implants having a first width size or circumference, a second width size or circumference and a third width size or circumference.

Referring now to FIG. 12, there is shown three prosthetic implants or a first prosthetic implant 300 having a first circumference (or diameter), a second prosthetic implant 302 having a second sized circumference (or diameter) and a third prosthetic implant 304 having a third sized circumference (or diameter) with each having a first dry size and a second larger hydrated size. In this embodiment, the marking 22a describes a hydrated size of the first prosthetic implant 300, the marking 22b describes a hydrated size of the second prosthetic implant 302 and the third marking 22c describes a hydrated size of the third prosthetic implant 304. It should be appreciated that although three sized circumferences are shown for the prosthetic implant (for illustration purposes only) it is envisioned that any number of prosthetic implant circumferences may be used in connection with the present disclosure such as five, six or ten different prosthetic implant circumferences.

In yet another embodiment, the markings 22a, 22b, 22c on the push rod 20 may simply describe a unit of measurement such as millimeters, centimeters, or inches, or a unit of volume. In one embodiment, there may be four different Implant sizes with the sizes being in terms of an implant diameter by a an implant height with the four different sizes being 20 mm by 30 mm, 22.5 mm by 30 mm, 22.5 mm by 32.5 mm, and 25 mm by 35 mm. Various configurations are possible and within the scope of the present disclosure.

Referring again to FIG. 11, the end effector 22 in one embodiment may be made from a radiopaque material, or a material that does not allow x-rays or radiation to pass through the end effector 22 for imaging purposes. It is envisioned that the surgeon in connection with the device 10 may take at least one image to assist with sizing of the cavity 200. The end effector 22 may be made from a suitable radiopaque material such as a radiopaque metal, and be configured for imaging so the surgeon can readily distinguish in the amount of the tissue that has been already removed and/or an amount of tissue that needs to be removed. The images may be taken from several different locations such as from an anterior location, a posterior location, or a lateral location. It is envisioned that images from several different locations may be taken.

Such radiopaque materials may include gold, platinum, tantalum, tungsten, iridium, rhenium, or an alloy of two or more such materials, or a coating of such materials to increase radiopacity such as a radiopaque material layer on the end effector 22. In another alternative embodiment, the end effector 22 may be made from a non-radiopaque material that is impregnated with a radiopaque material such as tantalum. The impregnated radiopaque material may include beads, bearings, wire, tape, or another radiopaque material that is dispersed along an array to render the device 10 radiopaque.

Figure 13:
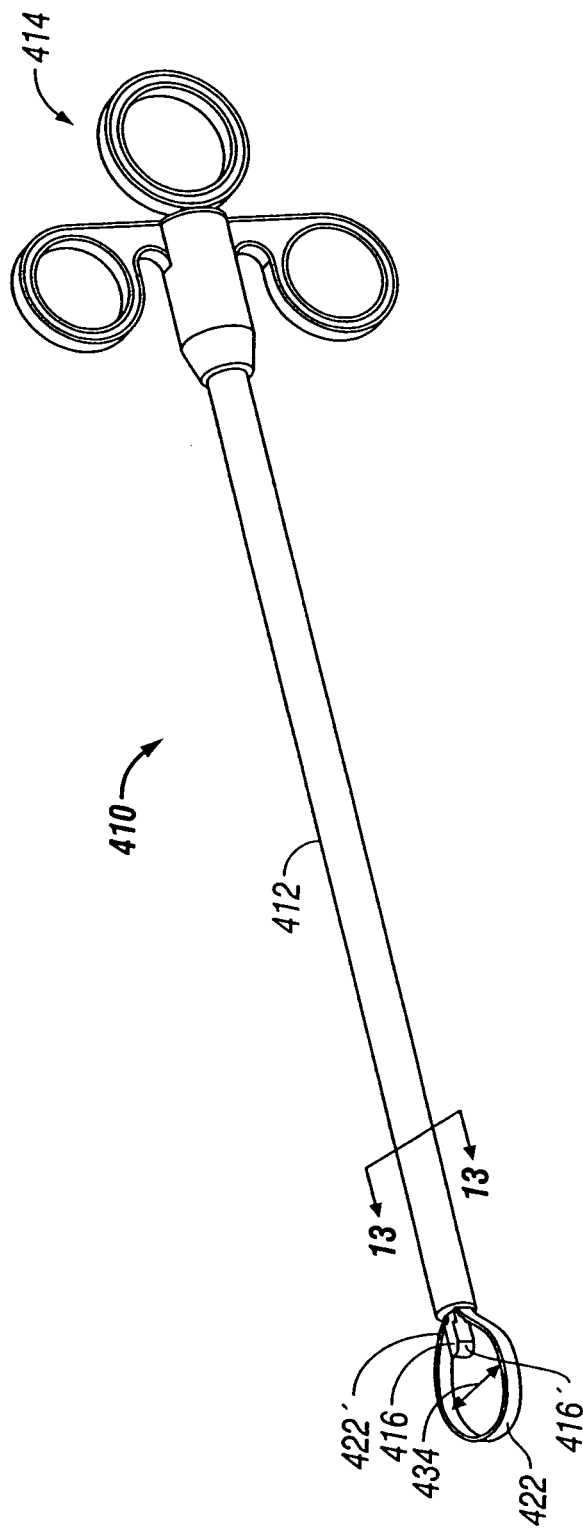
FIG. 13 is a perspective view of another embodiment of the device for determining a sufficiency of a cavity in an intervertebral disc space to receive a spinal nucleus implant of a predetermined dimension with the device having a distal nose assembly adapted to cooperate with and support the end effector.

FIGS. 13 through 20 illustrate another embodiment of the present device 10 generally represented by reference numeral 410. FIG. 13 shows a perspective view of the device 410 with a longitudinal body 412 and actuator portion 414 similar in function to the previously described embodiment. The device 410 determines sufficiency of the cavity in the intervertebral disc space to receive a spinal nucleus implant of a predetermined dimension generally similar to the embodiment of FIG. 1, however in this embodiment, the device 410 has a distal nose 416.

The distal nose 416 is located near the distal end of the longitudinal body 412 opposite the actuator portion 414. The distal nose 416 is formed in a cap like structure that covers and projects out of the distal opening of the longitudinal body 412. The distal nose 416 extends out of the longitudinal body 412 a fixed amount, but the distal nose 416 preferably does not extend or widen an overall width or diameter of the longitudinal body 412. This slim width permits the longitudinal body 412 to move freely and traverse through a cannula, tube or similar structure without any obstruction to permit the distal end of the device 410 to be readily delivered easily to a cavity for approximation purposes.

The distal nose 416 preferably may be made of a different or similar material than the remainder of the device 410. In one embodiment, the distal nose 416 may be made from a thermoplastic polymer or a biocompatible metal material such as titanium or stainless steel, and may be disposable. In another alternative embodiment, the distal nose 416 may be removed or separable from the device 410, e.g., a snap fit connection, by itself or together with the end effector 422. In this manner, at least one or both the distal nose 416 and the end effector 422 may be sterilized and reused while the remainder of the device 410 is discarded. Various configurations are possible and within the scope of the present disclosure.

The distal nose 416 has a curved surface 416'. The curved surface 416' is on the same side generally as the centermost portion of the longitudinal body 412. The opposite side or the side away from the centermost portion of the body 412 on the distal nose 416 is generally orthogonal shaped and is arranged to be substantially flush with the lateral side of the longitudinal body 412. The curved surface 416' is intended to permit the retraction and advancement of the end effector 422 without any obstruction or impairment of the movement of the end effector 422 during movement to the collapsed configuration or the expanded configuration. In a preferred embodiment, the distal nose 416 and surface 416' are adapted to receive the end effector 422 when the end effector 422 is in the retracted position. The curved shape of the surface 416' is configured to prevent the end effector 422 from kinking when it is retracted while keeping the effector 422 tightly bound within the dimensional confines of the diameter of the longitudinal body 412. The distal nose 416 may have other shapes, and is not limited to any particular shape, but in one embodiment, is configured to substantially seal the body 412 and permit the advancement and retraction of the end effector 422 in a quick and easy manner. Accordingly, the nose 416 may be configured to prevent or to impede bodily fluids from entering the device 410 that can interfere with movement of one or more components of the device 410 such as the push rod 420. An example of such a seal is discussed below with respect to FIG. 14.

Figure 14:
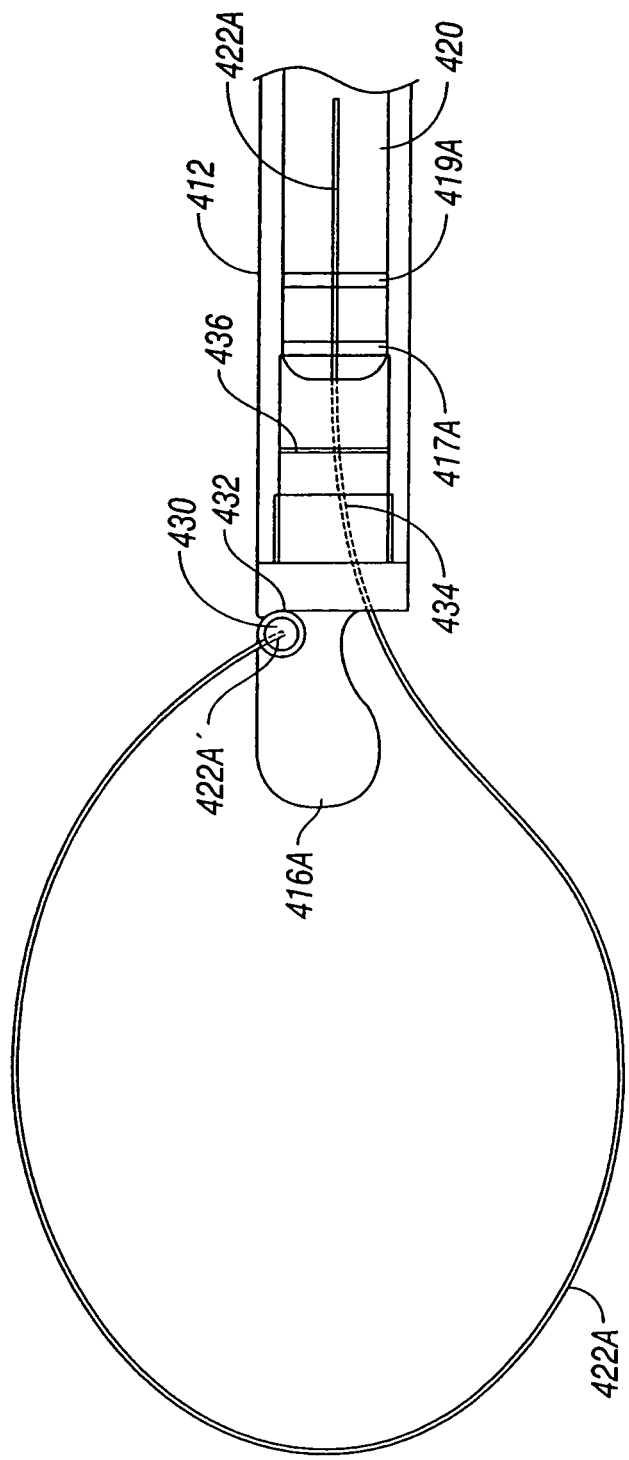
FIG. 14 is a top view in partial cross-section of the end effector and nose assembly of FIG. 13 showing one end of the end effector pivotally attached to the nose and the other end fixedly attached to a push rod.
Figure 15:
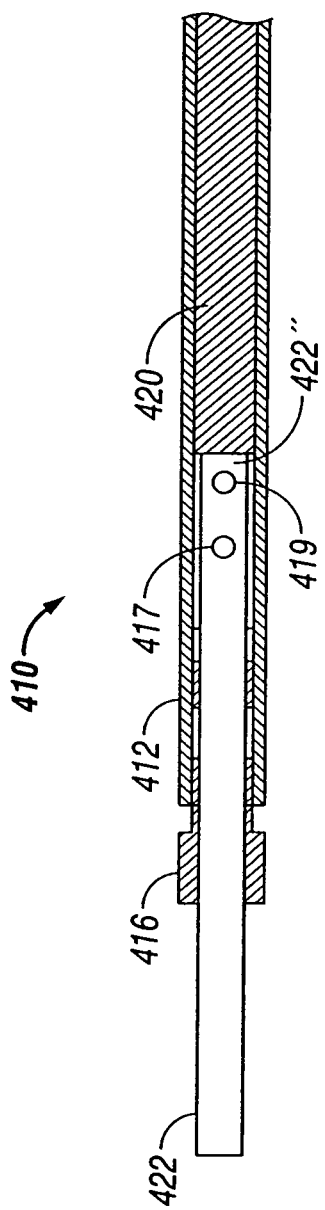
FIG. 15 is a cross sectional view of a portion of the device along line 13-13 of FIG. 13 showing the end effector having one end connected to a push rod.

Referring now to FIG. 15, there is shown a cross sectional view of the device 410 having the longitudinal body 412 shown with a lumen formed therethrough along line 13-13 of FIG. 12. In this embodiment, the device 410 has the end effector 422 which is a flexible looped ribbon-shaped member. In an alternative embodiment, the end effector 422 may be a braided cable or rope or have another configuration as described above. However, referring again to FIG. 13, the end effector or flexible member 422 is fixedly connected at one end 422' to the distal nose 416. The other end 422" of the flexible member 422 is connected to a push rod 420 (FIG. 14) by pins 417, 419. Alternatively, the end of the flexible member 422" may contain different numbers of pins, or be welded, adhered to, or friction fit to the push-rod 420. In this embodiment, the flexible end effector 422 is advantageously connected to the push rod 420 at one end 422" only for ease of operation. In this embodiment, the surgeon can easily manipulate the end effector 422 by manipulating the end effector 422 only at the end 422" using actuator 414 that is connected to the push rod 420. In an alternate embodiment, illustrated in FIG. 14, the effector 422A is attached to the nose 416A at one end 422A' via a cylinder 430 in socket 432 connection and is fixedly connected to the push rod 420 at the other end 422A". The end 422A" may be attached to the push-rod 420 by one or more pins 417A and 417B, by welding, adhesive, friction fit or any other suitable attachment means. The nose 416A is connected to the longitudinal body 412 by a snap fit connection which is preferably fluid-tight. Alternatively, the nose may be screwed into the distal end of the longitudinal body 412. The nose 416A includes a conduit 434 for slidably receiving and routing portions of the end effector 422A in or out of the distal end of the longitudinal body 412. The end of the end effector 422A is fixedly mounted to the push rod by pins 417A and 419A. A stop 436 is mounted within the lumen of the longitudinal body 412 to prevent the push rod 420 from impacting the nose 416A. The cylinder 430 and socket 432 connection allows the end 422A' to pivot as the end effector 422A is advanced or retracted and thus provide a greater degree of flexibility than a rigidly mounted end. Other pivotable connections are contemplated such as ball and socket and the like.

Figure 16:
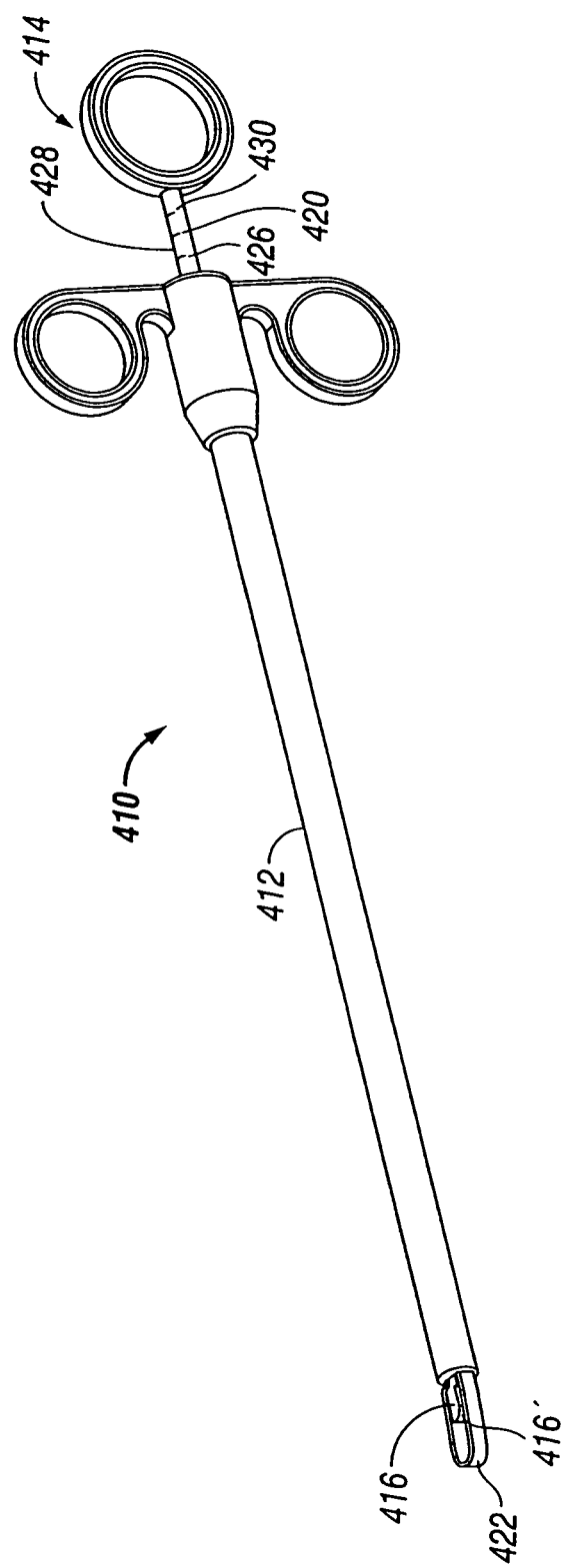
FIG. 16 is another perspective view of the device of FIG. 13 with the end effector partially retracted into the body of the device.

In the embodiments of FIGS. 13-20, the flexible end effector 422 or 422A can be manipulated distally and proximally by the push rod 420 simply by virtue of the connection at end 422" or 422A" while the end 422' or 422A' is connected to the distal nose 416 or 416A. Unless otherwise mentioned, the two embodiments relating to attachment of the end effector 422 or 422A discussed above, will be discussed interchangeably with respect to functionality of the embodiments while referring to the element numbers of the end effctor 422 embodiment for convenience. Referring now to FIG. 16, the end effector 422 can be manipulated at various intermediate positions therebetween by manipulating the actuator 414. The end effector 422 can be partially withdrawn in the device 410 and brought into close cooperative alignment with curved surface 416' of the distal nose 416, or in another position of operation the end effector 422 can be extended completely out of the device 410. In all arrangements, the end effector 422 can easily move from the collapsed configuration where the end effector 422 is in close cooperative alignment with the curved surface 416' of the distal nose 416 to the expanded configuration in continuous fashion.

Figure 17:
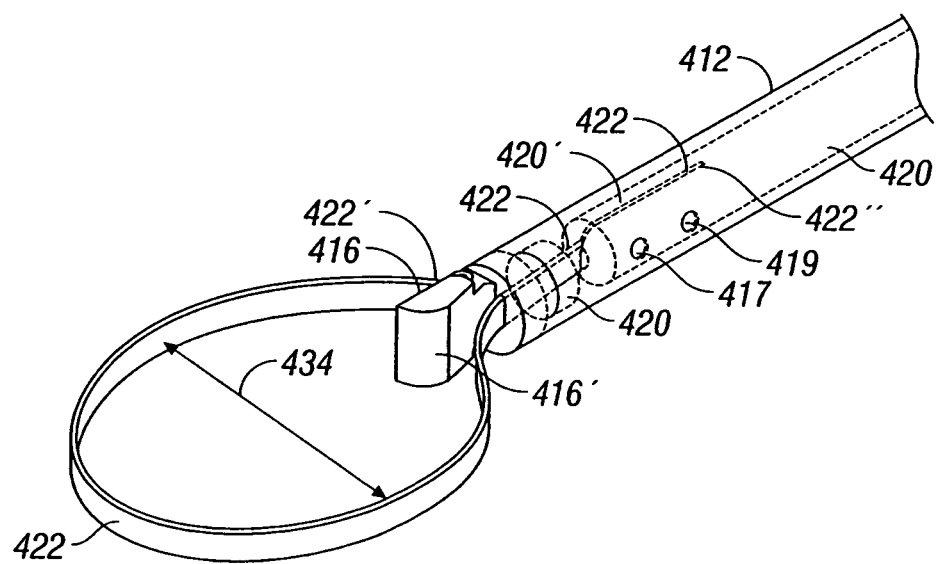
FIG. 17 is a close up perspective view of the end effector of FIG. 13 in an advanced position with the push rod partially shown in phantom dotted lines to show the contents thereof.

FIG. 17 illustrates a distal view of the end effector 422 connected to the push rod 420 which is rendered partially in phantom lines for illustration purposes. The end effector 422 is made of similar materials as discussed above and is sufficiently flexible so as to adjust a width 434 measured across the lateral sides or diameter (if the end effector 422 is circular) as shown in FIG. 17 simply by manipulating the actuator 414 (FIG. 13).

The end effector 422 is flexible and can be manipulated from a position where the end effector 422 is in close cooperative alignment with the surface 416' of the distal nose 416 (FIG. 17) to a maximum width or circumference. This maximum is when the end effector 422 is completely advanced outside of the body 412 (FIG. 13). The end effector 422 also can be adjustable to any other intermediate widths therebetween to approximate a cavity as discussed above. FIG. 17 illustrates the push rod 420 in a segmented fashion for illustration purposes. The push rod 420 is adapted to receive the end effector 422 through a channel 420' formed in the push rod 420. However, the end effector 422 can be directly connected to the push rod 420 or be made together with the push rod 420 as a single unitary member. In this illustrated embodiment, the end effector 422 is connected at the end 422" to the push rod 420 by pins 417, 419. However, it should be appreciated that the end effector 422 may be connected to push rod 420 by ultrasonic welding, fasteners, adhesive, or any other suitable connection.

On the other end 422' of the end effector 422, the end effector 422 may be fixedly secured to, or alternatively, be disposed through the distal nose 416 to secure end 422' to the distal nose 416. In another embodiment, the end effector 422 at end 422' may be fixedly connected alternatively to the longitudinal body 412, and not the distal nose 416. It should be appreciated that the end 422' is fixed and the distal nose 416 has a sloping surface 416' that allows the end effector 422 to be easily and quickly retracted into body 412 to a position where the end effector 422 is held substantially taught and pulled around curved surface 416' of distal nose 416. The pivotal connection (FIG. 14) was discussed above.

Figure 18:
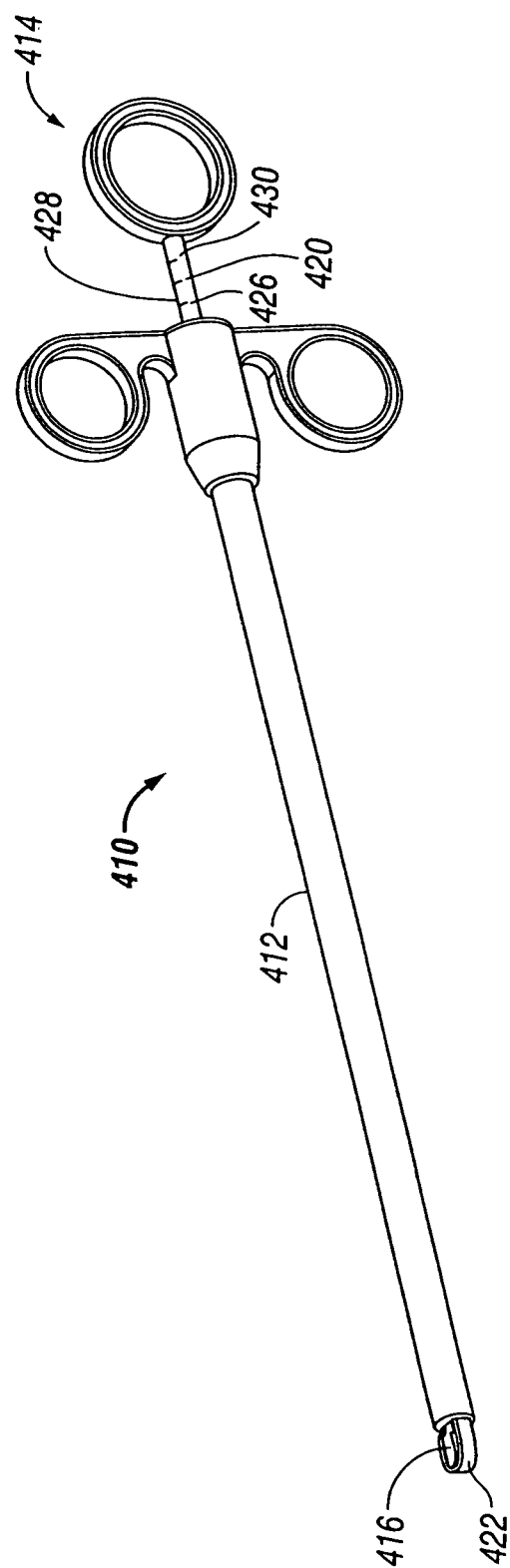
FIG. 18 is still another perspective view of the device for determining a sufficiency of a cavity in an intervertebral disc space to receive a spinal nucleus implant of a predetermined dimension with the device having the end effector in a retracted, collapsed configuration and in close cooperative alignment with the distal nose. Markings are shown at the proximal end of the push rod which correspond to predetermined circumference amounts of the end effector.

FIG. 13 and FIG. 18 show the device 410 in operation. FIG. 13 shows the device 410 having the end effector 422 in an expanded configuration. FIG. 13 illustrates that when the actuator 414 is manipulated to a distal position, the push rod 420 (FIG. 15) also moves distally which manipulates the end effector 422 to the expanded configuration. In this configuration, the end effector 422 is brought to a maximum circumference which may approximate a circumference of a cavity.

FIG. 18 illustrates the end effector 422 of the device 420 in a collapsed configuration. Here, the actuator 414 is manipulated in a proximal manner by the surgeon. The actuator 414, again, being connected to the push rod 420 draws the end effector 422 at end 422" proximally (FIGS. 15 and 17). The push rod 420 moves proximally to modulate or adjust the diameter 434 of the end effector 422 since end 422' or 422A' is fixed (FIGS. 14, 17). In the partially retracted position shown as FIG. 18, the end effector 422 or 422A is manipulated to be partially inside the longitudinal body 412. Moving in this configuration, the end effector 422 may approximate the circumference of a smaller sized cavity relative to FIG. 13, and the surgeon may read or observe which marking 426, 428, and 430 is visible on the proximal side of the push rod 420 and easily determine which of the prosthetic implants (FIG. 12) may fit in cavity 200 at this approximated circumference.

Figure 19:
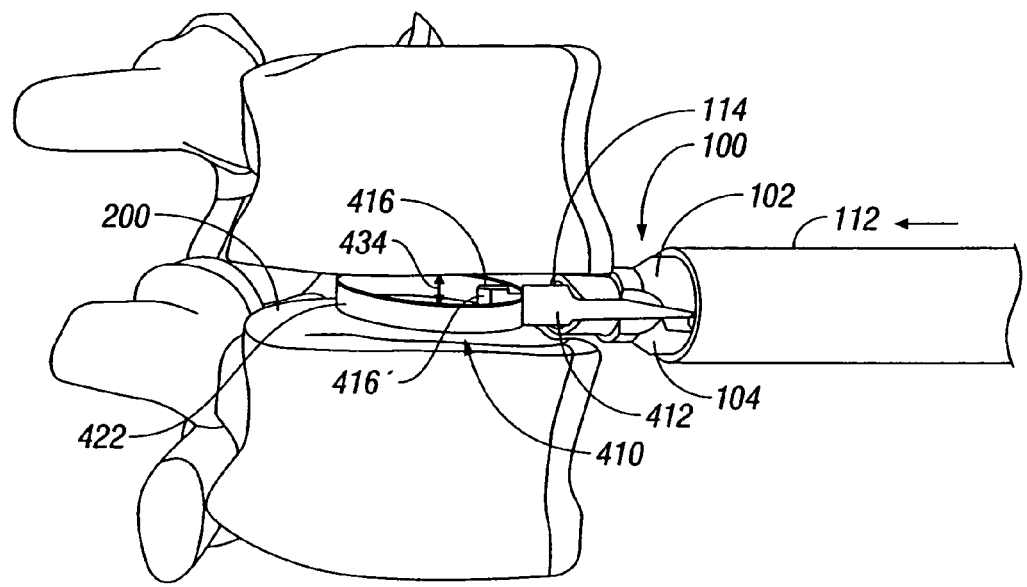
FIG. 19 is an enlarged view of the end effector of the device shown in FIG. 13 disposed in the spinal disc space for measuring the circumference of a cavity therein.
Figure 20:
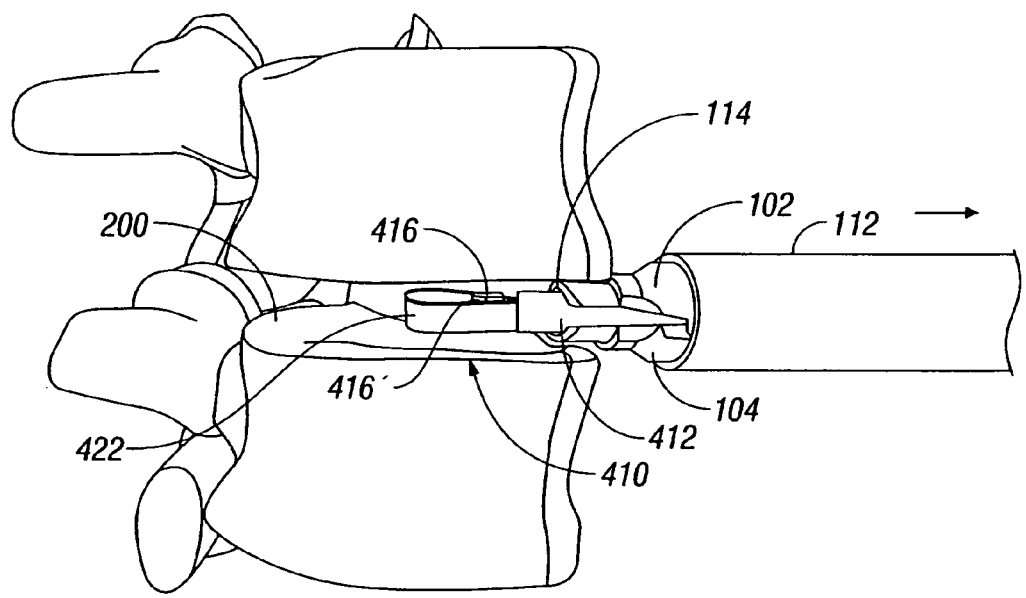
FIG. 20 is another enlarged view of the end effector shown in FIG. 19 in a partially retracted position.

FIGS. 19 through 20 illustrate the device 410 in operation in a surgical environment. Referring now to FIG. 19, there is shown the working tube 100 having the first member 102 and the second member 104 in a closed or approximated configuration with the closing tube 112 disposed over the working tube 100 as discussed with reference to FIGS. 6 through 11 above. The spreader 112 may be utilized as above. A lumen 114 is formed within the working tube 100 and the closing tube 112. As discussed above, the lumen 114 provides access to the operative site or cavity 200 through opening (not shown) on a proximal side. On the distal side, the distraction space is preserved by the closing tube 112 being placed in a coaxial alignment with the working tube 100.

The distal end of the device 410 is introduced through the lumen 114 as discussed previously. Once the distal end of the body 412 reaches the operative site or cavity 200, the end effector 422 can be introduced into the cavity 200 from a position where the end effector 422 is in close cooperative alignment with the curved surface 416' of the distal nose 416 to the expanded configuration. In other words, the end effector 422 once introduced in the cavity 200 goes from a configuration where the end effector 422 is in close cooperative alignment with the curved surface 416' to the expanded configuration to approximate the cavity.

This is advantageous since the end effector 422 has a reduced width when the end effector 422 is in close cooperative alignment with the curved surface 416' of the distal nose 416. In this configuration, the end effector 422 can travel distally through the working and closing tubes 100, 112 with ease. Once the end effector 422 is located in the cavity 200 and driven distally by moving the actuator (not shown) distally, the end effector 422 will contact the remaining nucleus pulposus or the lateral walls of the cavity to approximate one or more dimensions of the cavity 200. In a preferred embodiment, the end effector 422 measures whether enough tissue of the nucleus pulposus has been removed by a cavitation procedure to approximate the cavity. The device 410, thus, determines a sufficiency of the cavity 200 to receive a spinal nucleus implant of a predetermined dimension. As mentioned, the end effector 422 may itself be radiopaque or may be impregnated with radiopaque material so the surgeon can take images of the cavity 200.

The end effector 422 can then be selectively adjusted by the surgeon to increase its width/circumference and contact either the lateral side walls of the cavity 200 or the amount of the nucleus pulposus that remains in the cavity 200 (which is not shown for illustration purposes). The surgeon using the device 410 can then determine a sufficiency of a cavity 200 in an intervertebral disc space and whether the cavity 200 is sufficiently sized to receive a spinal nucleus implant of a predetermined dimension and whether a specific prosthetic implant having a predetermined circumference will fit into the cavity 200. If no implant is approximated to fit, the surgeon can easily and quickly remove the device 410 and then remove an additional amount of the nucleus pulposus remaining in the cavity 200. This is all accomplished advantageously by the surgeon without having a direct line of sight into the cavity 200.

FIG. 20 illustrates the end effector 422 manipulated proximally or in a direction toward the collapsed or retracted configuration. This is advantageous since at the conclusion of the approximation, and at the conclusion of the imaging, the end effector 422 may be withdrawn and brought into close cooperative alignment with the curved surface 416' of the distal nose 416 of the device 410. In this manner, the end effector diameter 434 is reduced substantially (relative to FIG. 19 showing the expanded configuration) without kinking the end effector 422 while keeping any exteriorly disposed portion of the end effector 422 secured to the nose 416. In this manner, the distal end of the device 410 can be easily removed through the working and closing tubes 100, 112, and then the correct prosthetic implant delivered to the excised disc space.

While several embodiments of the disclosure have been shown in the drawings, it is not intended that the disclosure be limited thereto, as it is intended that the disclosure be as broad in scope as the art will allow and that the specification be read likewise. For example, while the disclosure has generally been directed to cavities within the spinal disc space, it is contemplated that any cavity of unknown circumferential dimension may be measured in accordance with the principles described herein. Therefore, the above description should not be construed as limiting, but merely as exemplifications of preferred embodiments.

What is claimed is:

1. A device for dimensioning a circumference of a cavity comprising:
    a body having a lumen and a distal aperture in communication with the lumen;
    a longitudinal member extending through the lumen having a distal end and a proximal end, the longitudinal member capable of slidable movement through the body between retracted and advanced positions;
    a flexible looped member adapted to conform to a circumference of a cavity, wherein the flexible member is operatively connected to the distal end of the longitudinal member such that upon retraction of the longitudinal member, the flexible member retracts into the lumen and when the longitudinal member is moved toward the advanced position, the flexible member is advanced out of the lumen and expands to conform to a dimension which approximates the circumference of the cavity, the proximal end of the longitudinal member having at least one marking, the marking corresponding to a predetermined circumference of the flexible member; and
    a pin extending through the lumen of the body proximate to the distal aperture, the pin positioned between two sides of the looped member, the pin adapted and configured to assist spreading of the looped member as the looped member is advanced out of the lumen.

2. A device according to claim 1, wherein the flexible member is resilient.

3. A device according to claim 1, wherein the flexible member is radiopaque.

4. A device according to claim 1, wherein the flexible member has a size complementary to the lumen of the body in the retracted position.

5. A device according to claim 1, wherein the marking further corresponds to a predetermined circumference of a prosthetic implant.

6. A device according to claim 5 wherein the prosthetic implant is a spinal nucleus implant.

7. A device according to claim 1, wherein as the longitudinal member is advanced from the retracted position to the expanded position, a flexible member circumference expands to contact a lateral side wall of the cavity to approximate the cavity, the flexible member circumference upon contacting the lateral side wall of the cavity corresponding to the marking on the proximal end of the longitudinal member, the marking corresponding to a predetermined prosthetic implant circumference such that the prosthetic implant is adapted to fit into the cavity.

8. A device according to claim 1, wherein the flexible member is made of a shape memory alloy.

9. A device according to claim 1, wherein the flexible member is made of a thermoplastic polymer.

10. A device according to claim 1, wherein the flexible member is made of an elastic wire.

11. A device according to claim 1, wherein the flexible member is made of a ribbon.

12. A device according to claim 1, wherein the flexible member in the retracted position has a substantially zero width and is disposed substantially in the lumen.

13. A device according to claim 1, wherein the longitudinal member has a proximal end with a plurality of markings, the plurality of markings each corresponding to a predetermined circumference of a plurality of prosthetic implants;
    wherein as the longitudinal member is advanced from the retracted configuration to the expanded configuration, a flexible member circumference expands to contact a lateral side wall of the cavity to approximate the cavity, the flexible member circumference upon contacting the lateral side wall of the cavity corresponding to at least one marking of the plurality of markings on the proximal end of the longitudinal member; and wherein the marking corresponding to the predetermined prosthetic implant circumference corresponds to at least one predetermined circumference of the plurality of prosthetic implants such that the predetermined prosthetic implant fits into the cavity.

14. A device according to claim 13, wherein the flexible member is operatively connected to the distal end of the longitudinal member and in the advanced position, the flexible member has a circumference that is complementary to a largest prosthetic implant circumference of the plurality of prosthetic implants and wherein the flexible member in the retracted position has a width of about 0.1 mm.

15. A device according to claim 1, further comprising an actuator connected to the longitudinal member at the proximal end.

16. A device according to claim 1, wherein the flexible member is disposable.

17. A device according to claim 1, wherein the flexible member is connected to the distal end of the longitudinal member by a pin.

18. A device according to claim 1, wherein the flexible member has a thickness of about 0.1 mm to about 0.25 mm.

19. A device according to claim 1, wherein the cavity is located in a spinal disc space.

20. A device for dimensioning a circumference of a cavity according to claim 1, further comprising: a distal nose disposed at said distal aperture.

21. A device according to claim 20, wherein the distal nose has a curved surface, and wherein upon retraction of the longitudinal member the flexible member retracts partially into the lumen, and into close cooperative alignment with the curved surface.

22. A device according to claim 20, wherein the second end of the flexible member is connected to the distal nose.

23. A device according to claim 22 wherein the flexible member is pivotally connected to the distal nose.

24. A device according to claim 23, wherein the flexible member is pivotally connected to the distal nose by a cylinder and socket connection.

25. A device according to claim 20, wherein the longitudinal member includes a distal channel in communication with said distal aperture, the flexible member extending into the distal channel and connected to the longitudinal member in the distal channel.

26. A device according to claim 20, wherein the distal nose is removably attached to the distal aperture.

27. A device according to claim 26, wherein a portion of the distal nose is adapted and configured to form a substantially fluid tight seal with the distal aperture.

28. A device according to claim 20, wherein the distal nose is adapted and configured to prevent kinking of the flexible member when the flexible member retracts partially into the lumen.

29. A device according to claim 20, wherein the flexible member is made of a shape memory alloy.

30. A device according to claim 1, wherein the body is adapted and configured to fit within an access member.

31. A device according to claim 30, wherein the access member is selected from the group consisting of cannula, trocar, and working tube.

32. A device for dimensioning a circumference of a cavity comprising:
a body having a lumen and a distal aperture in communication with the lumen;
a longitudinal member extending through the lumen having a distal end and a proximal end, the longitudinal member capable of slidable movement through the body between retracted and advanced positions;
a flexible looped member adapted and configured to adjustably conform to a circumference of a cavity within an intervertebral disc space, wherein the flexible member is operatively connected to a longitudinal member such that upon retraction of the longitudinal member the flexible member retracts into the lumen;
wherein when the longitudinal member is moved toward the advanced position, the flexible member is advanced out of the lumen and assumes an expanded configuration to conform to a dimension which approximates the circumference of the cavity;
a pin extending through the lumen of the body proximate to the distal aperture, the pin positioned between two sides of the looped member, the pin adapted and configured to assist spreading of the looped member as the looped member is advanced out of the lumen;
wherein the longitudinal member has a proximal end with at least one marking, the marking corresponding to a predetermined circumference of a prosthetic implant;
wherein as the longitudinal member is advanced from the retracted configuration to the expanded configuration, the circumference of the flexible member increases and the flexible member contacts a lateral side wall of the cavity, the flexible member circumference upon contacting the lateral side wall of the cavity corresponding to the marking on the proximal end of the longitudinal member.

33. A device according to claim 32, wherein the marking corresponds to the predetermined circumference of a hydrated prosthetic implant.

34. A device according to claim 33, wherein the longitudinal member has a plurality of markings at the proximal end, each of said markings respectively corresponding to one of a plurality of prosthetic implants having different respective predetermined circumferences.

35. A device according to claim 32, wherein the flexible member is a looped member that is made from a radiopaque material.

36. An apparatus for dimensioning a circumference of a cavity comprising comprising:
(i) a device including a body having a lumen and a distal aperture in communication with the lumen, the body being adapted and configured to fit within an access member;
a longitudinal member extending through the lumen, the longitudinal member having a distal end and a proximal end; and
a flexible member adapted and configured to conform to a circumference of a cavity in a surgical site, wherein the flexible member is operatively connected to the longitudinal member such that manipulation of the longitudinal member causes the flexible member to conform to a dimension which approximates the circumference of the cavity; and
(ii) a tubular access member adapted and configured to receive the device and provide a conduit for the device to communicate with the surgical site, wherein the tubular access member is a working tube having a first longitudinal half member and a second longitudinal half member, the first member and second member being pivotally connected to one another such that approximation of the first member to the second member forms a tube having a lumen.

37. An apparatus according to claim 36, wherein the longitudinal member is capable of slidable movement through the body between retracted and advanced positions.

38. An apparatus according to claim 37, wherein upon retraction of the longitudinal member, the flexible member retracts into the lumen of the body and when the longitudinal member is moved toward the advanced position, the flexible member advances out of the lumen and expands to conform to a dimension which approximates the circumference of the cavity.

39. An apparatus according to claim 38, wherein the flexible member has a size complementary to the lumen of the body in the retracted position.

40. An apparatus according to claim 36, wherein the tubular access member is selected from the group consisting of cannula and trocar.

41. An apparatus according to claim 36, wherein the working tube has a distal end and a proximal end, the distal end adapted and configured to function as a distractor.

42. An apparatus according to claim 41, wherein the first member includes an upper jaw and the second member includes an opposing lower jaw which open when the first member and second member are brought into approximation.

43. An apparatus according to claim 41, wherein the distractor is adapted and configured to distract adjacent vertebrae of a spine.

44. An apparatus according to claim 36 wherein the flexible member is a looped member.

45. An apparatus according to claim 44, wherein the looped member is made of a shape memory alloy.

46. An apparatus according to claim 44, wherein the looped member is radiopaque.

47. An apparatus according to claim 36, further comprising an actuator connected to the longitudinal member at the proximal end.

48. An apparatus according to claim 36, wherein the body includes a distal nose disposed at said distal aperture.

49. An apparatus according to claim 48, wherein the distal nose has a curved surface, and wherein upon retraction of the longitudinal member the flexible member retracts partially into the lumen, and into close cooperative alignment with the curved surface.

50. An apparatus according to claim 48, wherein the flexible member has first and second ends, the flexible member being operatively connected to the longitudinal member at the first end and operatively connected to the body or the distal nose at the second end such that upon retraction of the longitudinal member, the flexible member retracts partially into the lumen and when the longitudinal member is moved toward the advanced position, the flexible member is advanced out of the lumen and expands to conform to a dimension which approximates a circumference of the cavity.

51. An apparatus according to claim 50, wherein the first end is operatively connected to the longitudinal member by a connection selected from the group consisting of one or more pins, welding, adhesive, friction and combinations thereof.

52. An apparatus according to claim 50, wherein the flexible member is pivotally connected to the body or the distal nose.

53. An apparatus according to claim 52, wherein the second end of the flexible member is connected to the distal nose.

54. An apparatus according to claim 53, wherein the flexible member is pivotally connected to the distal nose by a cylinder and socket connection.

55. An apparatus according to claim 50, wherein the longitudinal member includes a distal channel in communication with said distal aperture, the flexible member extending into the distal channel and connected to the longitudinal member in the distal channel.

56. An apparatus according to claim 48, wherein the distal nose is removably attached to the distal aperture.

57. An apparatus according to claim 48, wherein a portion of the distal nose is adapted and configured to form a substantially fluid tight seal with the distal aperture.

58. An apparatus according to claim 48, wherein the distal nose is adapted and configured to prevent kinking of the flexible member when the flexible member retracts partially into the lumen.

59. An apparatus according to claim 36, wherein the proximal end of the longitudinal member has at least one marking, the marking corresponding to a predetermined circumference of the flexible member.

60. An apparatus according to claim 59, wherein the marking further corresponds to a predetermined circumference of a prosthetic implant.

61. A method for determining a circumference of a cavity comprising:
   providing a cavity;
   providing a device comprising a body having a lumen, and a distal aperture in communication with the lumen;
   the device further comprising a longitudinal member extending through the lumen having a distal end and a proximal end, the longitudinal member capable of slidable movement through the body between retracted and advanced positions; and
   the device further comprising a flexible member adapted to conform to a circumference of a cavity, wherein the flexible member is operatively connected to the longitudinal member such that upon retraction of the longitudinal member, the flexible member retracts into the lumen and when the longitudinal member is moved toward the advanced position, the flexible member is advanced out of the lumen and expands to conform to a dimension which approximates the circumference of the cavity;
   advancing the flexible member into the cavity; and
   determining the circumference of the flexible member, wherein the circumference of the flexible member corresponds to the circumference of the cavity.

62. A method for determining a circumference of a cavity according to claim 61 further comprising:
   providing an access member which provides access to the cavity;
   inserting the device according to claim 61 into the access member; and
   advancing the flexible member into the cavity.

63. A method for determining a circumference of a cavity according to claim 62, wherein the access member is a tube having a lumen.

64. A method for determining a circumference of a cavity according to claim 63, wherein the tube having a lumen is selected from the group consisting of cannula and trocar.

65. A method for determining a circumference of a cavity according to claim 62 wherein the access member is a working tube which incorporates a distractor for separating adjacent vertebrae and the cavity is located within a spinal disc space.

66. A method for determining a circumference of a cavity according to claim 65, wherein the method further comprises distracting two adjacent vertebrae with the distractor.

67. A method for determining a circumference of a cavity according to claim 65 further comprising providing a spreader which is adapted and configured to be inserted into the access member, the spreader further adapted and configured to assist and support the separating function of the distractor.

68. A method for determining a circumference of a cavity according to claim 61, wherein the flexible member is a looped member.

69. A method for determining a circumference of a cavity according to claim 61, wherein the flexible member is operatively connected to the distal end of the longitudinal member and the proximal end of the longitudinal member has at least one marking corresponding to a predetermined circumference of the flexible member, such that determining the circumference of the flexible member includes observing the position of the at least one marking on the proximal end of the longitudinal member.

\* \* \* \* \*